US006982277B2

(12) United States Patent
Gudkov et al.

(10) Patent No.: US 6,982,277 B2
(45) Date of Patent: *Jan. 3, 2006

(54) P53 INHIBITORS AND THERAPEUTIC USE OF THE SAME

(75) Inventors: Andrei V. Gudkov, Glencoe, IL (US); Pavel G. Komarov, Oak Park, IL (US); Elena A. Komarova, Oak Park, IL (US)

(73) Assignee: The Board of Trutees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/350,560

(22) Filed: Jan. 24, 2003

(65) Prior Publication Data

US 2003/0144331 A1 Jul. 31, 2003

Related U.S. Application Data

(62) Division of application No. 09/493,527, filed on Jan. 28, 2000, now Pat. No. 6,593,353.

(60) Provisional application No. 60/117,881, filed on Jan. 29, 1999.

(51) Int. Cl.
    *A61K 31/425* (2006.01)
(52) U.S. Cl. .................................. 514/367
(58) Field of Classification Search ................ 514/367
    See application file for complete search history.

(56) References Cited

U.S. PATENT DOCUMENTS

| 4,497,817 | A | 2/1985 | Murase |
| 5,919,808 | A | 7/1999 | Petrie et al. |
| 6,372,249 | B1 * | 4/2002 | Smith et al. ............... 424/450 |
| 2002/0006941 | A1 * | 1/2002 | Gudkov et al. ............ 514/366 |
| 2002/0019425 | A1 * | 2/2002 | Gudkov et al. ............ 514/366 |
| 2003/0176318 | A1 * | 9/2003 | Gudkov et al. ............ 514/1 |

FOREIGN PATENT DOCUMENTS

| EP | 0430334 | 6/1991 |
| JP | 7291976 | 11/1995 |
| JP | 11029475 | 2/1999 |
| JP | 11103640 | 4/1999 |
| WO | WO 96/28454 | 9/1996 |
| WO | WO 98/17267 | 4/1998 |

OTHER PUBLICATIONS

V. A. Botchkarev et al., *Cancer Research.* 60, pp. 5002-5006 (2000).
M. V. Chernov et al., *Oncogene,* 14, 2503-2510 (1997).
Komarova et al., *Oncogene,* 17, pp. 1089-1096 (1998).
Andreani et al., *Journal of Medicinal Chemistry,* vol. 38, pp. 1090-1097 (1995).
Balse et al., *Indian Journal of Chemistry.* vol. 19B, pp. 263-265 (1980).
Singh et al., *Indian J. Chem.,* vol. 14B, pp. 997-998 (1976).
Naito et al., *J. Heterocyclic Chem.,* 34, pp. 1763-1767 (1997).
Kochergin et al., *J. Gen. Chem. U.S.S.R.,* 26, pp. 483-489 (1980).
P.G. Komarov et al., *Science,* 285, pp. 1733-1737 (1999).
K.K. Bhargava et al., *Journal of Medicinal Chemistry.* 20, No. 4, pp. 563-566 (1977).
C.L. Baird et al., *Inorganica Chimica Acta,* 256, pp. 253-262 (1997).
S. Tasaka et al., *J. Heterocyclic Chemistry,* 34, pp. 1763-1767 (1997).
S.N. Sawhney et al., *Indian J. Chem.,* 16B, pp. 523-524 (1978).
E.A. Komarova et al., *Seminars in Cancer Biology,* 8, No. 5, pp. 289-400 (1998).
R.J.C. Steele et al., *British Journal of Surgery.* 85, pp. 1460-1467 (1998).
E.A. Komarova et al., *The EMBO Journal,* 16, No. 6, pp. 1391-1400 (1997).

* cited by examiner

Primary Examiner—Christopher S. F. Low
Assistant Examiner—C. Delacroix-Muirheid
(74) Attorney, Agent, or Firm—Marshall, Gerstein & Borun LLP

(57) ABSTRACT

The therapeutic use of temporary p53 inhibitors in the treatment of p53-mediated diseases, conditions, and injuries is disclosed.

5 Claims, 13 Drawing Sheets

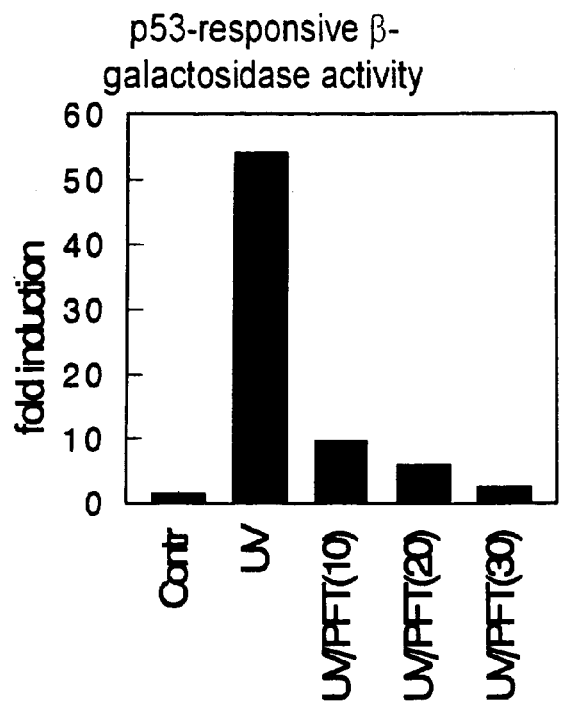
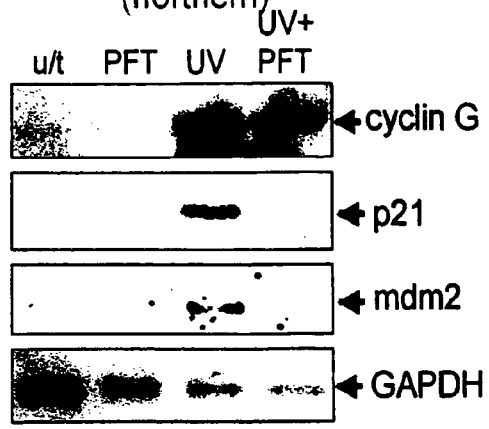
FIG. 2a p53-responsive β-galactosidase activity
FIG. 2b Natural p53 targets (northern)
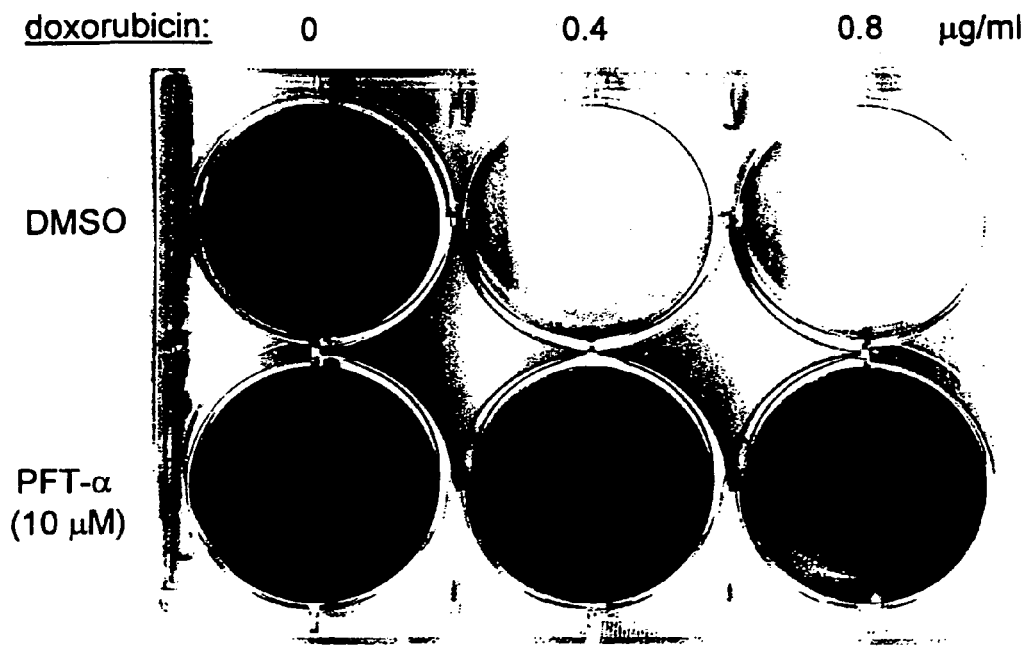
FIG. 3

SAOS cells
48h after transfection

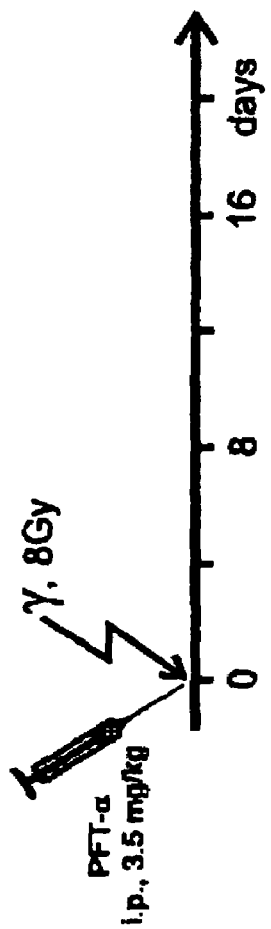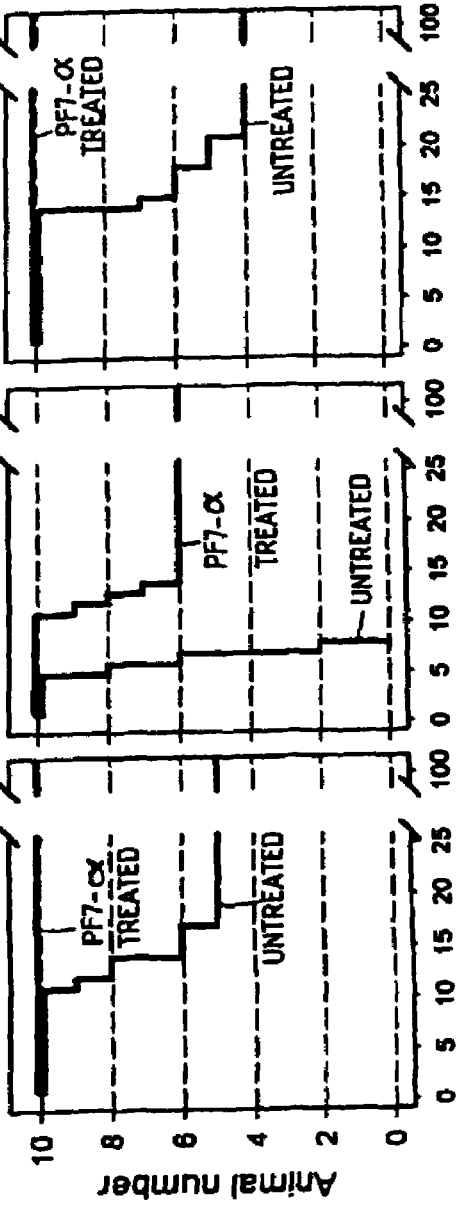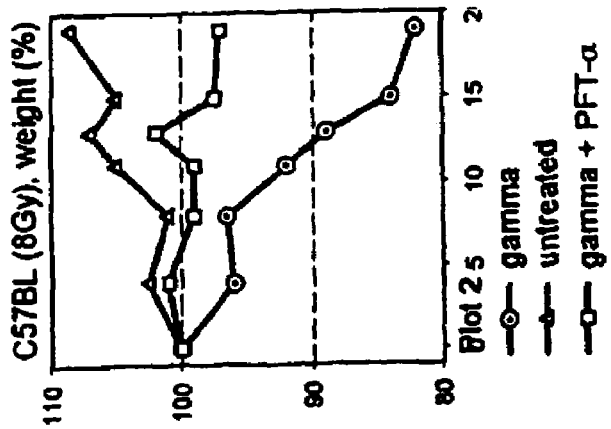

Small intestine
(8Gy, 24h)

Pifithrin-α increases resistance of C8 cells and sensitizes A4 to Taxol and AraC

Effect of PFTβ on LLC tumor response to cyclophosphamide in C57BL mice

P53 INHIBITORS AND THERAPEUTIC USE OF THE SAME

CROSS REFERENCE TO RELATED APPLICATIONS

This application is a divisional of application Ser. No. 09/493,527, filed Jan. 28, 2000, now U.S. Pat. No. 6,593,353, which claims the benefit of provisional application Ser. No. 60/117,881, filed Jan. 29, 1999.

FIELD OF THE INVENTION

The present invention relates to temporary p53 inhibitors and their use in therapy, for example, in cancer treatment, in modifying tissue response to a stress, and in modifying cell aging. More particularly, the present invention relates to compounds having the ability to effectively and temporarily inhibit p53 activity, and that can be used therapeutically, alone or in conjunction with a therapy, like chemotherapy or radiation therapy during cancer treatment, to treat a disease or condition where temporary inhibition of p53 activity provides a benefit. Examples of compounds that temporarily inhibit p53 activity and can be used therapeutically have the following general structural formulae (I) through (IV):

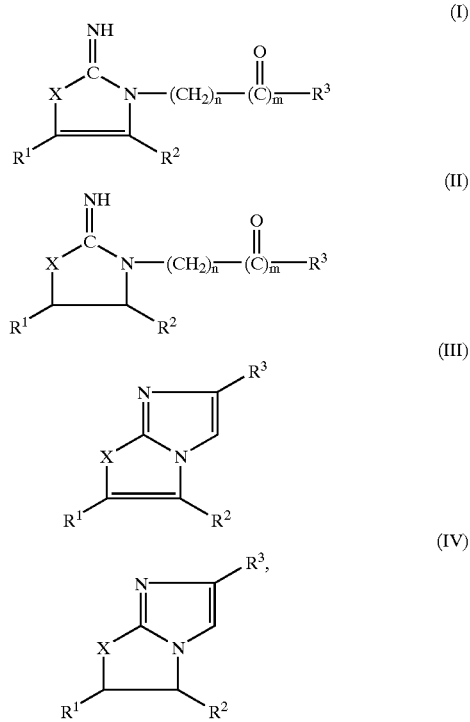

and pharmaceutically acceptable salts and hydrates thereof.

BACKGROUND OF THE INVENTION

The p53 gene is one of the most studied and well-known genes. p53 plays a key role in cellular stress response mechanisms by converting a variety of different stimuli, for example, DNA damage, deregulation of transcription or replication, and oncogene transformation, into cell growth arrest or apoptosis (T. M. Gottlieb et al., *Biochem. Biophys. Acta,* 1287, p. 77 (1996)).

p53 has a short half-life, and, accordingly, is continuously synthesized and degraded in the cell. However, when a cell is subjected to stress, p53 is stabilized. Examples of cell stress that induce p53 stabilization are:

a) DNA damage, such as damage caused by UV (ultraviolet) radiation, cell mutations, chemotherapy, and radiation therapy;

b) hyperthermia; and c) deregulation of microtubules caused by some chemotherapeutic drugs, e.g., treatment using taxol or Vinca alkaloids.

When activated, p53 causes cell growth arrest or a programmed, suicidal cell death, which in turn acts as an important control mechanism for genomic stability. In particular, p53 controls genomic stability by eliminating genetically damaged cells from the cell population, and one of its major functions is to prevent tumor formation.

p53 is inactivated in a majority of human cancers (A. J. Levine et al., *Br. J. Cancer,* 69, p. 409 (1994) and A. M. Thompson et al., *Br. J. Surg.,* 85, p. 1460 (1998)). When p53 is inactivated, abnormal tumor cells are not eliminated from the cell population, and are able to proliferate. For example, it has been observed that p53-deficient mice almost universally contract cancer because such mice lack a gene capable of maintaining genomic stability (L. A. Donehower et al., *Nature,* 356, p. 215 (1990) and T. Jacks et al., *Curr. Biol,* 4, p. 1 (1994)). A loss or inactivation of p53, therefore, is associated with a high rate of tumor progression and a resistance to cancer therapy.

p53 also imparts a high sensitivity to several types of normal tissue subjected to genotoxic stress. Specifically, radiation therapy and chemotherapy exhibit severe side effects, such as severe damage to the lymphoid and hematopoietic system and intestinal epithelia, which limit the effectiveness of these therapies. Other side effects, like hair loss, also are p53 mediated and further detract from cancer therapies. These side effects are caused by p53-mediated apoptosis, which maps tissues suffering from side effects of cancer therapies. Therefore, to eliminate or reduce adverse side effects associated with cancer treatment, it would be beneficial to inhibit p53 activity in normal tissue during treatment of p53-deficient tumors, and thereby protect normal tissue.

However, loss of p53 activity in tumors is associated with faster tumor progression and resistance to cancer treatment. Therefore, conventional theories dictate that suppression of p53 would lead to disease progression and protection of the tumor from a cancer therapy. Consequently, prior investigators attempted to restore or imitate the function of p53 in the prevention or treatment of a cancer.

Inactivation of p53 has been considered an undesirable and unwanted event, and considerable effort has been expended to facilitate cancer treatment by restoring p53 function. However, p53 restoration or imitation causes the above-described problems with respect to damaging normal tissue cells during chemotherapy or radiation therapy. These normal cells are subjected to stress during cancer therapy, which leads the p53 in the cell to cause a programmed death. The cancer treatment then kills both the tumor cells and the normal cells. A discussion with respect to suppression of p53 in various therapies is set forth in the publication, E. A. Komarova and A. V. Gudkov, "Could p53 be a target for therapeutic suppression?," *Seminars in Cancer Biology,* Vol. 8(5), pages 389–400 (1998), incorporated herein by reference.

In summary, p53 has a dual role in cancer therapy. On one hand, p53 acts as a tumor suppressor by mediating apoptosis and growth arrest in response to a variety of stresses and controlling cellular senescence. On the other hand, p53 is responsible for severe damage to normal tissues during cancer therapies. As disclosed herein, the damage caused by p53 to normal tissue made p53 a potential target for therapeutic suppression. In addition, because more than 50% of human tumors lack functional p53, suppression of p53 would not affect the efficacy of a treatment for such tumors, and would protect normal p53-containing tissues.

The adverse effects of p53 activity on an organism are not limited to cancer therapies. p53 is activated as a consequence of a variety of stresses associated with injuries (e.g., burns) naturally occurring diseases (e.g., hyperthermia associated with fever, and conditions of local hypoxia associated with a blocked blood supply, stroke, and ischemia) and cell aging (e.g., senescence of fibroblasts), as well as a cancer therapy. Temporary p53 inhibition, therefore, also can be therapeutically effective in: (a) reducing or eliminating p53-dependent neuronal death in the central nervous system, i.e., brain and spinal cord injury, (b) the preservation of tissues and organs prior to transplanting, (c) preparation of a host for a bone marrow transplant, and (d) reducing or eliminating neuronal damage during seizures, for example.

Activated p53 induces growth arrest, which often is irreversible, or apoptosis, thus mediating damage of normal tissues in response to the applied stress. Such damage could be reduced if p53 activity is temporarily suppressed shortly before, during, or shortly after, a p53-activating event. These and other p53-dependent diseases and conditions, therefore, provide an additional area for the therapeutic administration of temporary p53 inhibitors.

p53 also plays a role in cell aging, and, accordingly, aging of an organism. In particular, morphological and physiological alterations of normal tissues associated with aging may be related to p53 activity. Senescent cells that accumulate in tissues over time are known to maintain very high levels of p53-dependent transcription. p53-dependent secretion of growth inhibitors by senescent cells accumulate in aging tissue. This accumulation can affect proliferating cells and lead to a gradual decrease in overall proliferative capacity of tissues associated with age. Suppression of p53 activity, therefore, is envisioned as a method of suppressing tissue aging.

However, there are several important objectives that should be satisfied before a therapy involving suppression of p53 is implemented, for example:

(i) providing a p53 inhibitor that is sufficiently efficacious in vivo for practical administration as a therapeutic drug (i.e., inhibits p53 activity in a micromolar ($\mu$m) range of concentrations);

(ii) providing a p53 inhibitor that has a sufficiently low toxicity for use in therapy, and also does not cause undesirable side effects at concentrations sufficient to inhibit p53 activity;

(iii) exhibiting a p53 inhibition that is reversible because long-term p53 inactivation can significantly increase the risk of cancer;

(iv) during temporary p53 inhibition, the cells should recover from the applied stress and the p53-activating signal should be eliminated or reduced, otherwise restoration of p53 activity while the p53-activating signal is active could result in cell damage; and (v) the p53 suppression therapy is not associated with a dramatic increase in the frequency of cancer development, i.e., the therapeutic inhibitors target p53-mediated control of cellular response to stress, but do not affect p53-mediated control of oncogene transformation.

Until the present invention, p53 inhibitors useful in therapeutic applications have not been disclosed. A potential therapeutic inhibitor of p53 is a compound that acts at any stage of the p53 signaling pathway, and leads to functional inactivation of a p53-mediated response (i.e., blocking of p53-dependent growth arrest, apoptosis, or both). Prior investigators did not consider therapeutic p53 inhibitors because therapeutic p53 suppression was considered a disadvantage leading to the onset and proliferation of cancerous tumors. The present invention, therefore, is directed to the therapeutic and temporary inhibition of p53 activity, and to compounds capable of such inhibition.

SUMMARY OF THE INVENTION

The present invention is directed to the inhibition of p53 activity in therapeutic applications. The present invention also is directed to compounds that effectively and temporarily inhibit p53 activity, and to the therapeutic use of such temporary p53-inhibiting compounds.

Therefore, one aspect of the present invention is to provide p53 inhibitors that reversibly inhibit p53 activity and can be used therapeutically, for example, a compound having the general structural formulae (I) through (IV):

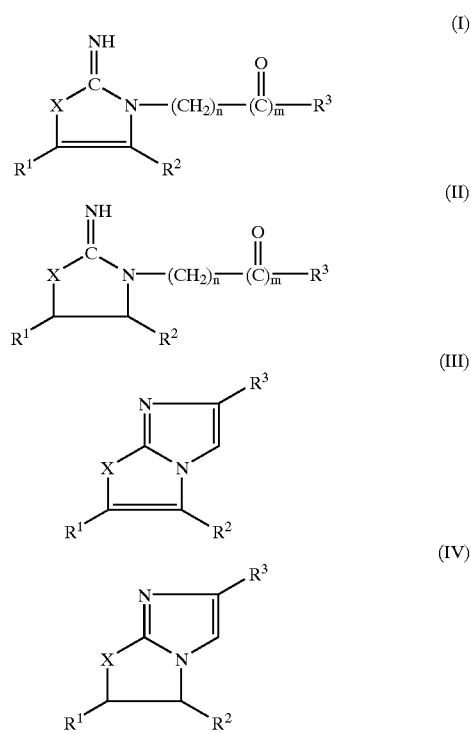

wherein X is O, S, or NH,
m is 0 or 1,
n is 1 to 4,
$R^1$ and $R^2$, independently, are selected from the group consisting of hydrogen, alkyl, alkenyl, alkynyl, aryl, aralkyl, alkaryl, a heterocycle, heteroaryl, heteroaralkyl, haloalkyl, haloaryl, alkoxy, aryloxy, alkoxyalkyl, aryloxyalkyl, aralkoxyalkyl, halo, (alkylthio)alkyl, (arylthio)alkyl, and (aralkylthio)alkyl,
or $R^1$ and $R^2$ are taken together to form an aliphatic or aromatic, 5 to 8-membered ring, either carbocyclic or heterocyclic;

R³ is selected from the group consisting of hydrogen, alkyl, haloalkyl, alkenyl, alkynyl, aryl, aralkyl, haloaryl, heteroaralkyl, a heterocycle, alkoxy, aryloxy, halo, $NR^4R^5$, $NHSO_2NR^4R^5$, $NHSO_2R^4$, and $SO_2NR^4R^5$; and R⁴ and R⁵, independently, are selected from the group consisting of hydrogen, alkyl, aryl, heteroaryl, and a heterocycle, or R⁴ and R⁵ are taken together to form an aliphatic or aromatic, 5- to 8-membered ring, either carbocyclic or heterocyclic; and pharmaceutically acceptable salts and hydrates thereof.

Another aspect of the present invention is to provide a method of reducing or eliminating death of normal cells attributable to treatment of a disease or condition comprising administering a therapeutically effective amount of a temporary p53 inhibitor to a mammal to reversibly inhibit p53 activity.

Yet another aspect of the present invention is to provide a method of reducing or eliminating normal cell death attributable to a trauma or contraction of a disease comprising administering a therapeutically effective amount of a temporary p53 inhibitor to a mammal to reversibly inhibit p53 activity.

Another aspect of the present invention is to provide a method of reducing or eliminating damage to normal tissue attributable to a treatment for a p53-deficient cancer comprising administering a therapeutically effective amount of a temporary p53 inhibitor to a mammal to reversibly inhibit p53 activity.

Still another aspect of the present invention is to provide an improved cancer treatment composition comprising:

(a) a chemotherapeutic drug, and
(b) a temporary p53 inhibitor.

Another aspect of the present invention is to provide an improved method of treating cancer comprising administration of a sufficient radiation dose to a mammal to treat a cancer, and administration of a therapeutically effective amount of a temporary p53 inhibitor to the mammal to reversibly inhibit p53 activity.

Another aspect of the present invention is to provide a method of preventing cell death attributable to a stress-inducing event effecting the cell, said method comprising treating the cell with a therapeutically effective amount of a compound capable of reversibly inhibiting p53 activity in the cell.

Another aspect of the present invention is to provide a pharmaceutical composition for treating a disease comprising (a) a drug capable of treating the disease, and
(b) a temporary p53 inhibitor.

Another aspect of the present invention is to provide a pharmaceutical composition comprising (a) a temporary p53 inhibitor, and
(b) a carrier.

Another aspect of the present invention is to provide a method of modulating tissue aging comprising treating the tissue with a therapeutically effective amount of a compound capable of reversibly inhibiting p53 activity.

Another aspect of the present invention is to provide a method of treating a mammal subjected to a dose of radiation comprising administering to the mammal of a therapeutically effective amount of a compound capable of reversibly inhibiting p53 activity to protect radiated mammal.

Yet another aspect of the present invention is to provide a method of sensitizing p53-deficient cells to a cancer therapy comprising administering a therapeutically effective amount of a compound capable of reversibly inhibiting p53 activity to a mammal, in conjunction with the cancer therapy, to destroy cells that otherwise are unaffected by the cancer therapy.

Another aspect of the present invention is to provide an improved method of treating cancer comprising administration of a therapeutically effective amount of a chemotherapeutic agent to a mammal to treat a cancer, and administration of a therapeutically effective amount of a temporary p53 inhibitor to the mammal to reversibly inhibit p53 activity, wherein the dose of the chemotherapeutic agent is greater than a dose of the identical chemotherapeutic agent required to treat the cancer in the absence of the p53 inhibitor.

These and other aspects of the present invention will become apparent from the following nonlimiting, detailed description of the preferred embodiments.

BRIEF DESCRIPTION OF THE FIGURES

FIGS. 2(a) and (b), respectively, show the dependence of β-galactosidase activity in UV-irradiated Con A cells at 10, 20, and 30 μM and PFT-α inhibition of p53-responsive genes;

FIG. 3 illustrates suppression of p53-dependent apoptosis by PFT-α administration;

FIGS. 7(a)–(d) contain plots of live animals vs. days after irradiation, and a plot of weight (%) vs. days after irradiation, for mice subjected to gamma radiation, and either treated or untreated with PFT-α;

DETAILED DESCRIPTION OF THE PREFERRED EMBODIMENTS

Figure 1:
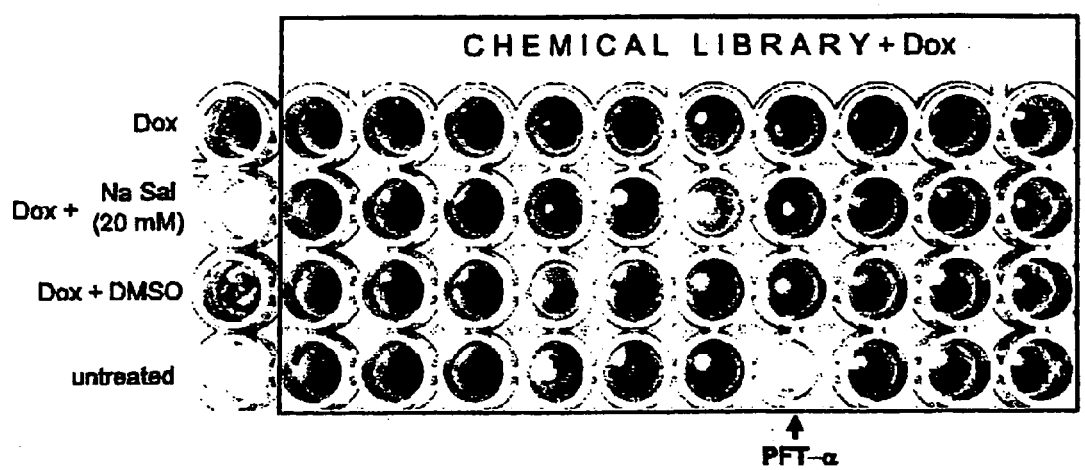
FIG. 1 illustrates screening of a chemical library for a p53 inhibitor.

As previously stated, the effectiveness of chemo- and radiation therapy has been limited by severe side effects to normal tissue, including injuries to hematopoietic and lymphoid systems, intestinal epithelia, and testicular cells.

Because p53 is involved in the induction of such injuries, p53 was investigated as a potential target for therapeutic suppression to decrease damage to normal tissue. p53 suppression therapy is especially useful in the treatment of tumors that lack functional p53, and therefore that cannot benefit from additional p53 suppression.

p53 performs an important function by eliminating damaged and potentially dangerous cells by forcing the cell to give its own life for the benefit of the entire cell society of the organism. Inhibiting p53 activity during cancer therapy could lead to the survival of genetically altered cells, which otherwise would be eliminated by p53-dependent growth arrest or apoptosis. Therefore, p53 suppression has an inherent danger that damaged cells will not self-destruct and, therefore, can proliferate. This can increase the risk of a new cancer induced by suppression of p53 activity.

It has been found that this inherent danger is offset by providing a temporary, or reversible, inhibition of p53 activity, which allows a damaged normal cell to repair itself during the period of p53 inhibition. When the effects of the p53 inhibitor have diminished or terminated, p53 then is available to perform its normal function. This mechanism is beneficial in cancer treatment, especially during the acute phase treatment of a p53-deficient cancer, wherein normal cells are affected during a cancer treatment, e.g., chemo- or radiation therapy. In turn, the severe adverse side-effects attributed to the cancer treatment are reduced or eliminated.

As also stated previously, a p53 inhibitor useful in therapy is efficacious at a low concentration, is low in toxicity, does not cause undesirable side effects at therapeutically effective concentrations, exhibits reversible, i.e., temporary, p53 inhibition, inhibits p53 for a sufficient time to allow normal cells to recover from an applied stress, and does not cause a significant increase in cancer development.

The term "temporary" or "reversible" inhibition of p53 activity as used herein means inhibition of p53 activity shortly after administration of a p53 inhibitor, e.g., about 5 minutes to about one hour after administration, and continuing for about 24 to about 96 hours after administration of the p53 inhibitor is completed.

In identifying useful therapeutic p53 inhibitors, an important consideration is that activation of p53 leads to transactivation of p53-responsive genes, and in some cell types results in apoptosis. Suppression of these effects can be used to identify therapeutic p53 inhibitors.

In particular, p53 acts as a nuclear transcription factor that activates or suppresses a number of p53-responsive genes through binding with specific DNA sequences. Transcriptional activation of p53-responsive reporter beta-galactosidase gene (LacZ) in transgenic mice maps the tissues affected to side effects of a cancer therapy. Cell lines expressing reporter genes (e.g., lacZ, luciferase, GFP, and secreted factors) under the control of p53-responsive promoters, therefore, can be used to screen compounds capable of either activating or suppressing p53 transcriptional regulation.

Specifically, a p53 wild-type Balb 3T3 cell line ConA that contains LacZ gene under the control of p53-responsive elements consisting of a p53-binding DNA consensus sequence, p53-binding site from ribosomal protein promoter in combination with minimal heat shock gene promoter was used. p53 activation in these cells by gamma irradiation, UV light, or treatment with various chemotherapeutic drugs leads to accumulation of beta-galactosidase that can be detected easily by routine X-gal staining.

This system has been used previously to identify the inhibition of p53 activity by sodium salicylate. Sodium salicylate, however, is not a viable candidate as a therapeutically useful p53 inhibitor because sodium salicylate is therapeutically effective only at high concentrations starting at 20 mM (millimolar). At this therapeutically effective concentration, and even at one-half of the effective concentration, sodium salicylate injections were lethal to all treated test animals.

A screening program to detect p53 inhibitors identified the following classes of compounds as possessing properties that make the compounds useful in therapeutic applications. In particular, the following classes of compounds effectively and reversibly inhibit p53 activation. As discussed in more detail hereafter, the compounds can be used alone, or, for example, in conjunction with chemotherapy or radiation therapy during cancer treatment, to protect normal cells from p53 programmed death due to stresses inflicted by a cancer treatment or by a disease or trauma. In addition, during chemotherapy, both tumor and normal cells are destroyed. Tumor cells are preferentially killed compared to normal cells, which is the basis of a successful chemotherapy. By administering a therapeutic p53 inhibitor, normal cells are protected, and the dose of the chemotherapeutic agent, therefore, can be increased to more effectively treat the cancer.

Examples of therapeutically effective, temporary p53 inhibitors have the general structural formulae (I) through (IV):

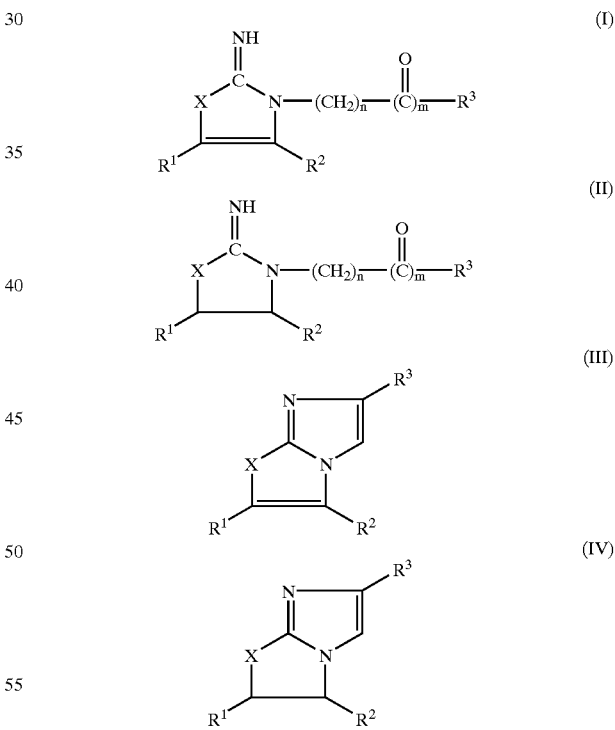

wherein X is O, S, or NH,
m is 0 or 1,
n is 1 to 4,
$R^1$ and $R^2$, independently, are selected from the group consisting of hydrogen, alkyl, alkenyl, alkynyl, aryl, aralkyl, alkaryl, a heterocycle, heteroaryl, heteroaralkyl, haloalkyl, haloaryl, alkoxy, aryloxy, alkoxyalkyl, aryloxyalkyl, aralkoxyalkyl, halo, (alkylthio)alkyl, (arylthio)alkyl, and (aralkylthio)alkyl, or $R^1$ and $R^2$ are taken together to form an aliphatic or aromatic, 5 to 8-membered ring, either carbocyclic or heterocyclic;

$R^3$ is selected from the group consisting of hydrogen, alkyl, haloalkyl, alkenyl, alkynyl, aryl, alkaryl, aralkyl, haloaryl, heteroaralkyl, a heterocycle, alkoxy, aryloxy, halo, $NR^4R^5$, $NHSO_2NR^4R^5$, $NHSO_2R^4$, and $SO_2NR^4R^5$; and $R^4$ and $R^5$, independently, are selected from the group consisting of hydrogen, alkyl, aryl, heteroaryl, and a heterocycle, or $R^4$ and $R^5$ are taken together to form an aliphatic or aromatic, 5- to 8-membered ring, either carbocyclic or heterocyclic; and pharmaceutically acceptable salts and hydrates thereof.

Compounds of formulae (I) through (IV) contain $R^1$ through $R^5$ groups that are unsubstituted or optionally substituted with one or more, and typically one to three, substituents. Suitable substituents include, but are not limited to, alkyl, aryl, OH, $NR^4R^5$, CN, $C(=O)NR^4R^5$, $SR^4$, $SO_2R^4$, $CO_2R^6$ (wherein $R^6$ is hydrogen or alkyl), $OC(=O)R^6$, $OR^6$, $CF_3$, halo, and $NO_2$.

As used herein, the term "alkyl," alone or in combination, is defined to include straight chain or branched chain saturated hydrocarbon groups from $C_1$–$C_8$. The term "lower alkyl" is defined herein as $C_1$–$C_4$. Examples of alkyl groups include, but are not limited to, methyl, ethyl, n-propyl, isopropyl, isobutyl, n-butyl, n-hexyl, and the like. The term "alkyl" also includes "cycloalkyl," which is defined herein to include cyclic hydrocarbon radicals from $C_1$–$C_7$. Examples of cycloalkyl radicals include, but are not limited to, cyclopropyl, cyclobutyl, and cyclopentyl. The terms "alkenyl" and "alkynyl" are defined similarly as "alkyl," but contain at least one carbon-carbon double bond or triple bond, respectively.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, phenyl, hydroxy, hydroxyalkyl, alkoxy, haloalkyl, nitro, amino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methylphenyl, biphenyl, 4-iodophenyl, 4-methoxyphenyl, 3-trifluoromethylphenyl, 4-nitrophenyl, and the like.

The term "haloaryl" and "haloalkyl" are defined herein as a previously defined alkyl or aryl group wherein at least one hydrogen atom has been replaced by a "halo" group as defined herein.

The term "heteroaryl" is defined herein as a 5-membered or 6-membered heterocyclic aromatic group, e.g., thienyl, furyl, or pyridyl, which optionally has a fused benzene ring, and which can be unsubstituted or substituted, for example, with one or more, and in particular one to three substituents, like halo, alkyl, hydroxy, alkoxy, haloalkyl, nitro, amino, acylamino, alkylthio, alkylsulfinyl, and alkylsulfonyl. Examples of heteroaryl groups include, but are not limited to, thienyl, furyl, pyridyl, benzoxazolyl, benzthiazolyl, benzisoxazolyl, oxazolyl, quinolyl, isoquinolyl, triazolyl, isothiazolyl, isoxazolyl, imidazolyl, pyrazinyl, pyrimidinyl, thiazolyl, thiadiazolyl, benzimidazolyl, indolyl, benzofuryl, and benzothienyl.

The term "aralkyl" is defined herein as a previously defined alkyl group, in which one of the hydrogen atoms is replaced by an aryl group as defined herein, for example, a phenyl group optionally having one or more substituents, for example, halo, alkyl, alkoxy, hydroxy, and the like. An example of an aralkyl group is benzyl.

The term "heteroaralkyl" is defined similarly as the term "aralkyl," however, the hydrogen is replaced by a heteroaryl group.

The term "alkaryl" is defined herein as a previously defined aryl group in which one of the hydrogen atoms is replaced by an alkyl group as defined herein, either substituted or unsubstituted. An example of an alkaryl group is 4-methylphenyl.

The terms "alkoxyalkyl" and "aryloxyalkyl" are defined as an alkyl group wherein a hydrogen has been replaced by an alkoxy group or an aryloxy group, respectively. The term "aralkoxyalkyl" is similarly defined wherein an aralkoxy group is substituted for a hydrogen of an alkyl group. The terms "(alkylthio)alkyl," "(arylthio)alkyl," and "(aralkylthio)allyl" are defined similarly as the three above groups, except a sulfur atom, rather than an oxygen atom, is present.

The term "halogen" or "halo" is defined herein to include fluorine, chlorine, bromine, and iodine.

The term "heterocycle" is defined as a $C_4$ to $C_8$ aliphatic ring system, preferably a $C_5$ to $C_6$ aliphatic ring system, containing one to three atoms selected from the group consisting of oxygen, sulfur, and nitrogen, with the remaining atoms being carbon. Examples of heterocycles include, but are not limited to, tetrahydrofuran, tetrahydropyran, morpholine, dioxane, piperidine, piperazine, pyrrolidine, and morpholine.

The terms "alkoxy" and "aryloxy" are defined as —OR, wherein R is alkyl or aryl.

The term "hydroxy" is defined as —OH.

The term "hydroxyalkyl" is defined as a hydroxy group appended to an alkyl group.

The term "amino" is defined as —$NH_2$, and the term "alkylamino" is defined as —$NR_2$ wherein at least one R is alkyl and the second R is alkyl or hydrogen.

The term "acylamino" is defined as RC(=O)N, wherein R is alkyl or aryl.

The term "nitro" is defined as —$NO_2$.

The term "alkylthio" is defined as —SR, where R is alkyl.

The term "alkylsulfinyl" is defined as R—$SO_2$, where R is alkyl.

The term "alkylsulfonyl" is defined as R—$SO_3$, where R is alkyl.

In preferred embodiments, X is S or NH; m is 1; n is 1 or 2; $R^1$ and $R^2$, independently, are hydrogen, alkyl, aryl, aralkyl, alkaryl, or are taken together to form a 5- or 6-membered, carbocyclic or heterocyclic ring; and $R^3$ is alkyl, aryl, alkaryl, aralkyl, haloaryl, or a heterocycle, and salts and solvates thereof.

In more preferred embodiments, the compound has a structural formula (I) or (III); X is S; m is 1; n is 1, $R^1$ and $R^2$ are taken together to form a 5- or 6-membered aliphatic carbocyclic ring; and $R^3$ is alkyl or phenyl, preferably substituted with halo (e.g., iodo), alkyl (e.g., methyl), or aryl (e.g., phenyl).

The therapeutic p53 inhibitors include all possible geometric isomers of compounds of structural formulae (I) through (IV). The p53 inhibitors also include all possible stereoisomers of compounds of structural formulae (II) and (IV) including not only racemic compounds, but also the optically active isomers as well. When a compound of structural formula (II) or (IV) is desired as a single enantiomer, it can be obtained either by resolution of the final product or by stereospecific synthesis from either isomerically pure starting material or any convenient intermediate.

Resolution of the final product, an intermediate, or a starting material can be achieved by any suitable method known in the art. Additionally, in situations where tautomers of the compounds of structural formulae (I) through (IV) are possible, the present invention is intended to include all tautomeric forms of the compounds. For example, a compound of structural formula (I), wherein m and n each are one, can exist in the following tautomeric form

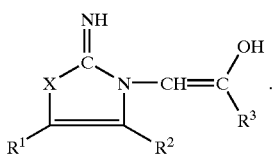

Compounds of structural formulae (I) through (IV) which contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the compounds of structural formulae (I) through (IV), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulphonate, and p-toluenesulphonate salts. In light of the foregoing, any reference to compounds of the present invention appearing herein is intended to include compounds of structural formulae (I) through (IV), as well as pharmaceutically acceptable salts and solvates thereof.

The compounds of structural formulae (I) through (IV) can be used to inhibit p53 in any organism that possesses the p53 gene. Typically, reversible p53 inhibition can be performed in a mammal, including humans. Therapeutically, a reversible p53 inhibitor, such as a compound of structural formulae (I) through (IV), can be administered to a mammal, in a therapeutically effective amount, to treat any disease, condition, or injury, wherein inhibition of p53 activity provides a benefit.

As set forth below, administration of a present p53 inhibitor to a mammal has several potential benefits, including, for example, rescuing damaged cells from death caused by cellular stress, which occurs in cancer treatments and hyperthermia; providing a method of treating individuals, like workers in nuclear power plants and in radiopharmaceuticals, subjected to potentially harmful radiation dosages; and modulating tissue aging attributed to senescent cells.

The temporary p53 inhibitors, like compounds of structural formulae (I) through (IV), can be therapeutically administered as the neat chemical, but it is preferable to administer compounds of structural formulae (I) through (IV) as a pharmaceutical composition or formulation. Accordingly, the present invention further provides for pharmaceutical formulations comprising, for example, a compound of structural formulae (I) through (IV), or pharmaceutically acceptable salts thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

The amount of a temporary p53 inhibitor required for use in therapy varies with the nature of the condition being treated, the length of time p53 suppression is desired, and the age and the condition of the patient, and is ultimately determined by the attendant physician. In general, however, doses employed for adult human treatment typically are in the range of 0.001 mg/kg to about 200 mg/kg per day. A preferred dose is about 1 µg/kg to about 100 µg/kg per day. The desired dose can be conveniently administered in a single dose, or as multiple doses administered at appropriate intervals, for example as two, three, four or more subdoses per day. Multiple doses often are desired, or required, because the suppression of p53 activity is temporary.

Formulations of the present invention can be administered in a standard manner, such as orally, parenterally, sublingually, transdermally, rectally, transmucosally, topically, via inhalation, or via buccal administration. Parenteral administration includes, but is not limited to, intravenous, intraarterial, intraperitoneal, subcutaneous, intramuscular, intrathecal, and intraarticular.

For veterinary use, a p53 inhibitor, in particular a compound of formulae (I) through (IV), or a nontoxic salt thereof, is administered as a suitably acceptable formulation in accordance with normal veterinary practice. The veterinarian can readily determine the dosing regimen and route of administration that is most appropriate for a particular animal.

A pharmaceutical composition containing a present p53 inhibitor can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol, or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical transdermal formulations comprise conventional aqueous or nonaqueous vehicles, such as creams, ointments, lotions, and pastes, or are in the form of a medicated plaster, patch, or membrane.

Additionally, compositions of the present invention can be formulated for parenteral administration by injection or continuous infusion. It is envisioned that injection or continuous infusion is the preferred method of administration. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for reconstitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (as an emulsion in an acceptable oil, for example), ion exchange resins, or as sparingly soluble derivatives (as a sparingly soluble salt, for example).

A temporary p53 inhibitor, like a compound of formulae (I) through (IV), also can be used in combination with other therapeutic agents which can be useful in the treatment of cancer and other conditions or disease states. The invention thus provides, in another aspect, a combination of a therapeutic, temporary p53 inhibitor together with a second therapeutically active agent.

A temporary p53 inhibitor, like a compound of formulae (I) through (IV), can be used in the preparation of a medicament for coadministration with the second therapeutically active agent in treatment of conditions where inhibition of p53 activity is beneficial. In addition, a temporary p53 inhibitor can be used in the preparation of a medicament for use as adjunctive therapy with a second therapeutically active compound to treat such conditions. Appropriate doses of known second therapeutic agents for use in combination with a temporary p53 inhibitor are readily appreciated by those skilled in the art.

For example, a therapeutic, temporary p53 inhibitor can be used in combination with a cancer therapy, such as radiotherapy or chemotherapy. In particular, a p53 inhibitor can be used in conjunction with chemotherapeutic drugs, such as cis-platin, doxorubicin, Vinca alkaloids, taxol, cyclophosphamide, ifosphamide, chlorambucil, busulfan, mechlorethamine, mitomycin, dacarbazine, carbo-platin, thiotepa, daunorubicin, idarubicin, mitoxanthrone, bleomycin, esperamicin $A_1$, dactinomycin, plicamycin, carmustine, lomustine, tauromustine, streptozocin, melphalan, dactinomycin, and procarbazine, for example. A therapeutic p53 inhibitor also can be used in combination with drugs used to treat stroke, ischemia, or blocked blood supplies; or in combination with drugs used to treat arthritis or diseases that cause hyperthermia.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination referred to above, therefore, can be administered either sequentially or simultaneously from the same or separate pharmaceutical formulations. As is the case for the present therapeutic p53 inhibitors, a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, a temporary p53 inhibitor, such as a compound of formulae (I) through (IV), and the second therapeutic agent are administered by the same route, either from the same or from different pharmaceutical compositions. However, in other embodiments, using the same route of administration for the therapeutic p53 inhibitor and the second therapeutic agent either is impossible or is not preferred. Persons skilled in the art are aware of the best modes of administration for each therapeutic agent, either alone or in a combination.

Generally, compounds of structural formulae (I) through (IV) can be prepared according to the following synthetic scheme disclosed in A. Andreani et al., *J. Med. Chem.*, 38, pp. 1090–1097 (1995), which is incorporated herein by reference. Compounds of structural formula (I) or (II), wherein n is 1, then can be converted into a compound of structural formula (III) or (IV). In the scheme disclosed in the Andreani et al. publication, it is understood in the art that protecting groups can be employed where necessary in accordance with general principles of synthetic chemistry. These protecting groups are removed in the final steps of the synthesis under basic, acidic, or hydrogenolytic conditions which are known and readily apparent to those skilled in the art. By employing appropriate manipulation and protection of any chemical functionalities, synthesis of compounds of structural formulae (I) through (IV) not specifically set forth herein can be accomplished by methods analogous to the schemes set forth below. Unless otherwise noted, all starting materials were obtained from commercial suppliers and used without further purification.

As disclosed in the Andreani et al. publication, the compounds of general structural formula (I) or (II), wherein X is S, can be prepared by reacting a 2-aminothiazole with a mole equivalent amount of a bromoketone compound in acetone at reflux for about 30 minutes. The reaction mixture then is cooled, and the product is isolated as the hydrobromide salt. Other compounds of formula (I) can be prepared identically by reacting a 2-aminoimidazole (X=NH) or a 2-aminooxazole (X=O) with a bromoketone. The reaction to provide a compound of structural formula (I), wherein X is S, is illustrated by the following:

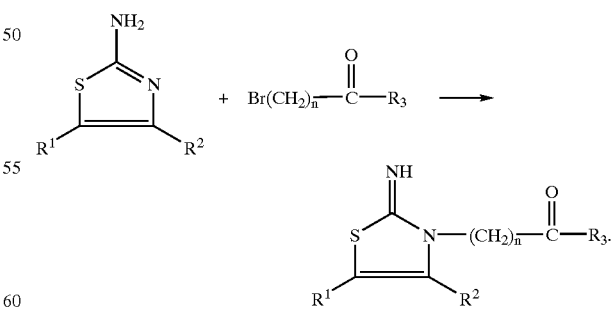

The same reaction can be used to provide a compound of structural formula (II), for example, by reacting 2-aminoimidazolidine with a bromoketone. Alternatively, a compound of structural formula (I) can be converted to a compound of structural formula (II).

A compound of structural formula (I) or (II), wherein m and n each are 1, can be converted into a compound of structural formula (III) or (IV), respectively. This conversion is achieved by heating a composition of structural formula (I) or (II) in a solvent, such as methanol, ethanol, or isopropyl alcohol, for a sufficient time, e.g., about 1 to about 10 hours, to cyclize the compound and yield a compound of structural formula (III) or (IV). In some cases, a compound of structural formula (I) or (II), in solution, slowly cyclizes to a compound of structural formula (III) or (IV) while standing at room temperature. The preparation of a compound of structural formulae (III) and (IV) from a compound of structural formulae (I) and (II) is illustrated below:

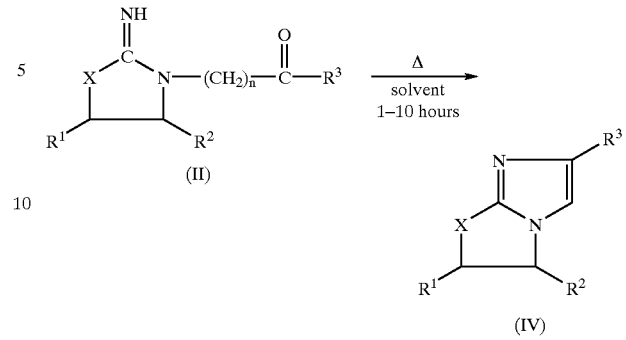

Particular compounds of structural formulae (I) and (III) were prepared by the following procedure:

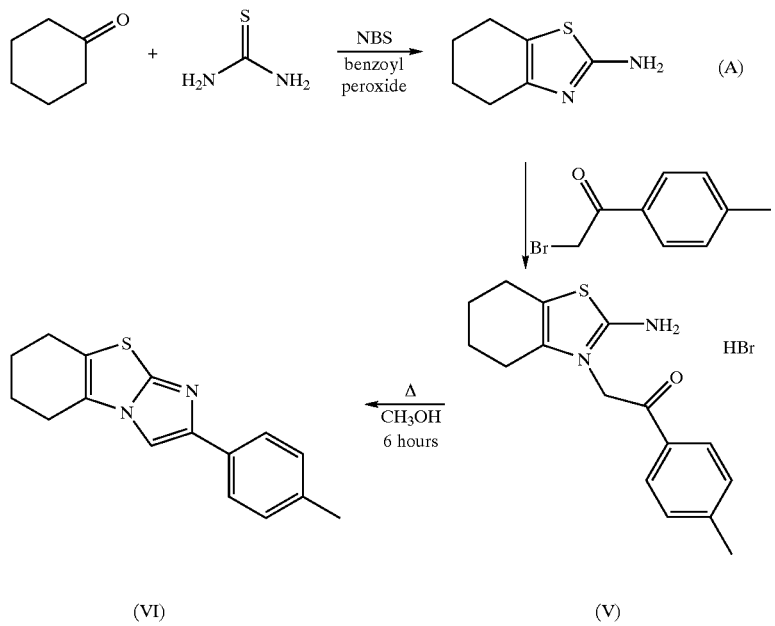

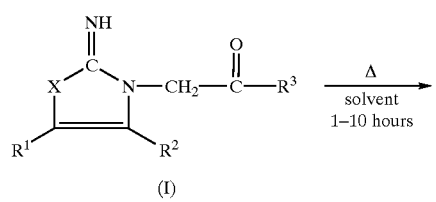

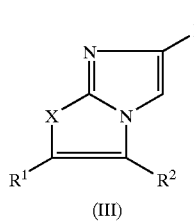

A reaction mixture containing cyclohexanone (1.96 g, 20 mmol), thiourea (1.52 g, 20 mmol), N-bromosuccinimide (NBS) (3.56 g, 20 mmol), and benzoyl peroxide (100 mg) in 40 ml of benzene was prepared, then heated at reflux overnight. The benzene then was removed under reduced pressure. The residue was dissolved in water, then neutralized with sodium carbonate. The resulting precipitate was filtered, vacuumed to dryness, and recrystallized from hexane to yield the 2-aminothiazole derivative A (1.81 g, yield 59%).

A solution of compound A (1.54 g, 10 mmol) and para-methylphenacyl bromide (2.34 g, 11 mmol) in 50 ml of benzene was prepared, then stirred at room temperature for 48 hours. Product (V) (a compound of structural formula (I) where X=S and n=1) precipitated from the reaction mixture, was filtered, and then washed with benzene to yield 2.42 g (66% yield) of the compound of structural formula (V). The compound of structural formula (V) was a stable, water-soluble compound.

A solution of compound (V) (1.10 g, 3.0 mmol) in 30 ml methanol was refluxed for 6 hours. The reaction mixture then was cooled, mixed with water, and neutralized with sodium carbonate. The resulting solid product was filtered from the mixture, vacuumed to dryness, and recrystallized from ethanol to provide 0.45 g (yield 56%) of compound (VI), i.e., a compound of structural formula (III).

These, and other specific, nonlimiting compounds encompassed by structural formulae (I) and (III) were synthesized and have the following structures:

(V)
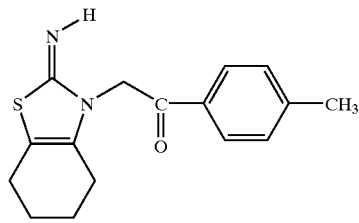

(VI)
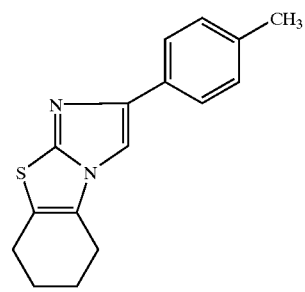

(VII)
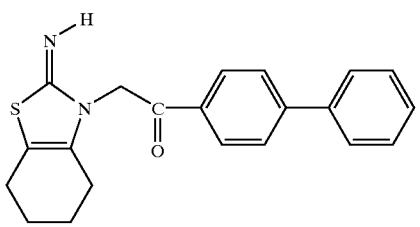

(VIII)
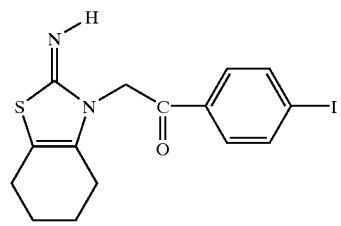

(IX)
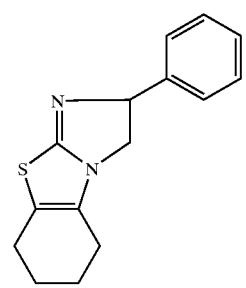

(X)
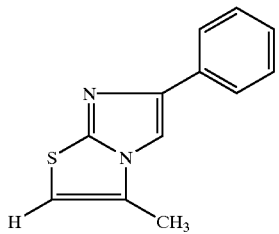

(XI)
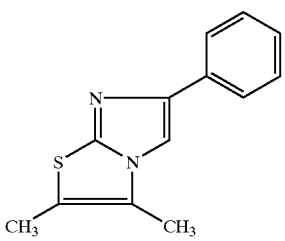

The compounds of structural formulae (V)–(XI) are named:

(V)—2-[2-imino-4,5,6,7-tetrahydro-1,3-benzothiazol-3(2H)-yl]-1-(4-methylphenyl)-1-ethanone;

(VI)—2-(4-methylphenyl)-5,6,7,8-tetrahydrobenzo[d]imidazo[2,1-b]thiazole;

(VII)—2-[2-imino-4,5,6,7-tetrahydro-1,3-benzothiazol-3(2H)-yl]-1-(4-iodophenyl)-1-ethanone;

(VIII)—2-[2-imino-4,5,6,7-tetrahydro-1,3-benzothiazol-3(2H)-yl]-1-(biphenyl)-1-ethanone;

(IX)—2-phenyl-5,6,7,8-tetrahydrobenzo-[ d]imidazo[2,1-b]thiazole;

(X)—3-methyl-6-phenylimidazo[2,1-b] -thiazole; and (XI)—2,3-dimethyl-6-phenylimidazo[2,1-b]thiazole;

respectively. The compound of structural formula (V) also is known by the trivial names of pifithrin-alpha and PFT-α. The compound of structural formula (VI) also is known by the trivial names pifithrin-beta and PFT-β. The compound of structural formula (VII) also is known as compound 86B10.

The compounds of structural formulae (V) and (VI) are disclosed in Balse et al., *Indian J. Chem.*, Vol. 19B, pp. 293–295 (April, 1980). The compound of structural formula (IX) is disclosed in Singh et al., *Indian J. Chem.*, Vol. 14B, pp. 997–998 (December, 1976) and in S. Naito et al., *J. Heterocyclic Chem.*, 34, pp. 1763–1767 (1997). The compounds of structural formula (X) and (XI) are disclosed in P. M. Kochergin et al., *J. Gen. Chem. U.S.S.R.*, 26, pp. 483–489 (1956).

The compounds of structural formulae (VII) and (VIII) were prepared in a scheme identical to compound (V) by using the appropriate α-bromo ketone, i.e., bromomethyl 4-(phenyl)ketone and bromomethyl 4-iodophenyl ketone, respectively. Other compounds of structural formulae (I) and (II) can be prepared in a similar manner using the appropriate thiazole, imidazole, or oxazole derivative and bromo ketone.

Compounds of structural formulae (I)–(IV) also were prepared by methods disclosed in the above-identified Balse et al. and Singh et al. publications. Accordingly, the following compounds of structural formulae (XII)–(XV) also can be utilized as temporary p53 inhibitors:

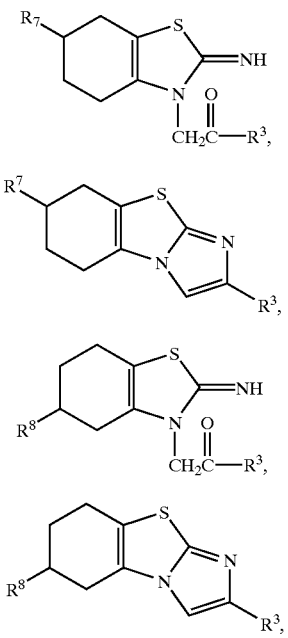

wherein $R^7$ is hydrogen or alkyl, $R^8$ is $CO_2R^6$ or hydrogen, and $R^3$ is selected from the group consisting of phenyl, 4-chlorophenyl, 4-nitrophenyl, 3-nitrophenyl, 4-methylphenyl, 4-phenylphenyl, and 4-bromophenyl. The 3-nitrophenyl derivative is disclosed in WO 98/17267.

An additional temporary p53 inhibitor of structural formulae (I)–(IV) has the following structure wherein $R^1$ and $R^2$ are taken together to form a 6-membered aromatic ring:

(XVI)

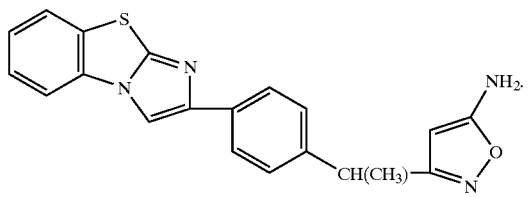

Additional compounds having a structural formula (III), wherein X is S, are disclosed in JP 11-106340 and JP 7-291976, incorporated herein by reference.

The ability of compounds of structural formulae (I) through (IV) to inhibit p53 activity, both effectively and reversibly, and their use as therapeutic agents was demonstrated in the following tests and experiments.

To demonstrate the ability of a temporary p53 inhibitor, like a compound of structural formulae (I) through (IV), to suppress p53 activity, a p53 activator (e.g., doxorubicin or gamma irradiation) was applied directly to ConA cells followed by X-gal staining. Then, a p53 inhibitor was applied in a concentration of 1 μM to 20 μM to the test cells in the presence of the p53 activator. Cytotoxicity of the p53 inhibitors also was determined by standard assays. An estimation of antiapoptotic activity of the p53 inhibitor compounds was based on an ability to suppress apoptotic cell death in standard cell systems sensitive to p53-dependent apoptosis (i.e., mouse embryonic fibroblasts transformed with Ela+ras, line C8, described by S. W. Lowe et al., Cell, 74, pp. 957–968 (1993)). p53 dependence of the compound activity was analyzed by testing its effect on p53-deficient cells (i.e., radiosensitivity or drug sensitivity of p53−/− mouse embryonic fibroblasts transformed with Ela+ras, line A4, described by Lowe et al., 1993).

The results of these tests are illustrated in attached FIGS. 1–16. These figures, in general, are based on tests performed on compounds of structural formulae (V) and (VI). In the following Figures, test results illustrated for compound (V), i.e., PFT-α, were repeated for compound (VI), i.e., PFT-β. Test results using PFT-β were essentially identical to test results using PFT-α.

FIG. 1 illustrates screening a chemical library for suppression of p53-dependent transcriptional activation. In the screening test, ConA cells (mouse Balb 3T3 cells expressing bacterial lacZ gene under the control of p53-responsive promoter, as described in E. A. Komarova et al., EMBO J., 16, pp. 1391–1400 (1997)), were plated in 96-well plates and treated for 24 hours with 0.2 μg/ml of doxorubicin (i.e., a p53-activating chemotherapeutic drug, also known as adriamycin) in combination with test compounds at concentrations of about 10 to about 20 μM. DMSO (dimethyl sulfoxide) and sodium salicylate were used as negative and positive controls, respectively (left column). Cells were fixed and stained by a standard X-gal procedure to monitor lacZ expression. The well containing pifithrin-alpha is identified by the arrow in FIG. 1, and illustrates the effectiveness of PFT-α in inhibiting p53.

PFT-α also blocked activation of p53-responsive lacZ in ConA cells induced by ultraviolet (UV) light in a dose-dependent manner, as illustrated in FIG. 2. In particular, FIG. 2(a) shows that PFT-α, at 10, 20, and 30 μM, affects β-Gal activity in UV-irradiated (25 J/m²) ConA cells. The cells were collected 8 hours after UV treatment, and β-Gal expression in the extracts was estimated by a standard colorimetric assay. (See, for example, V. A. Tron et al., Am. J. Pathol., 153, p. 597 (1998).)

FIG. 2(b) shows that PFT-α inhibits UV-induced transactivation of cyclin G, p21/waf1, mdm2, and GAPDH, which are known p53-responsive genes. FIG. 2(b) contains Northern blots of RNA from ConA cells as follows: u/t, untreated; PFT, incubated for 8 hours with 10 mM of PFT-α; UV, 8 hours after UV treatment (25 J/m²); UV+PFT, a combination of PFT treatment (10 mm) and UV treatment.

However, to be useful therapeutically, a p53 inhibitor must possess the properties of (a) efficacy at a low concentration, (b) low toxicity, (c) an absence of adverse side effects, (d) reversible p53 inhibition, (e) p53 inhibition for a sufficient time to allow cells to recover from an applied stress, and (f) not causing a dramatic increase in cancer development.

FIG. 3 illustrates that pifithrin-alpha suppresses p53-dependent apoptosis caused by doxorubicin. Equal numbers of mouse embryo fibroblasts transformed with El+ras (line C8, highly sensitive to p53-dependent apoptosis) were plated in the wells of 6-well plates containing 0, 0.4, and 0.8 μg/ml of doxorubicin, treated with DMSO and PFT-α (10 μM) for 48 hours, fixed with methanol, and stained with crystal violet, followed by elution of the dye with 1% SDS. Optical density (530 μM) was determined using a BioTek EL311 microplate reader. The intensity of staining reflects the number of surviving cells. The results show that at 10 μM PFT-α inhibited apoptotic death of C8 cells induced by doxorubicin.

Figure 10:
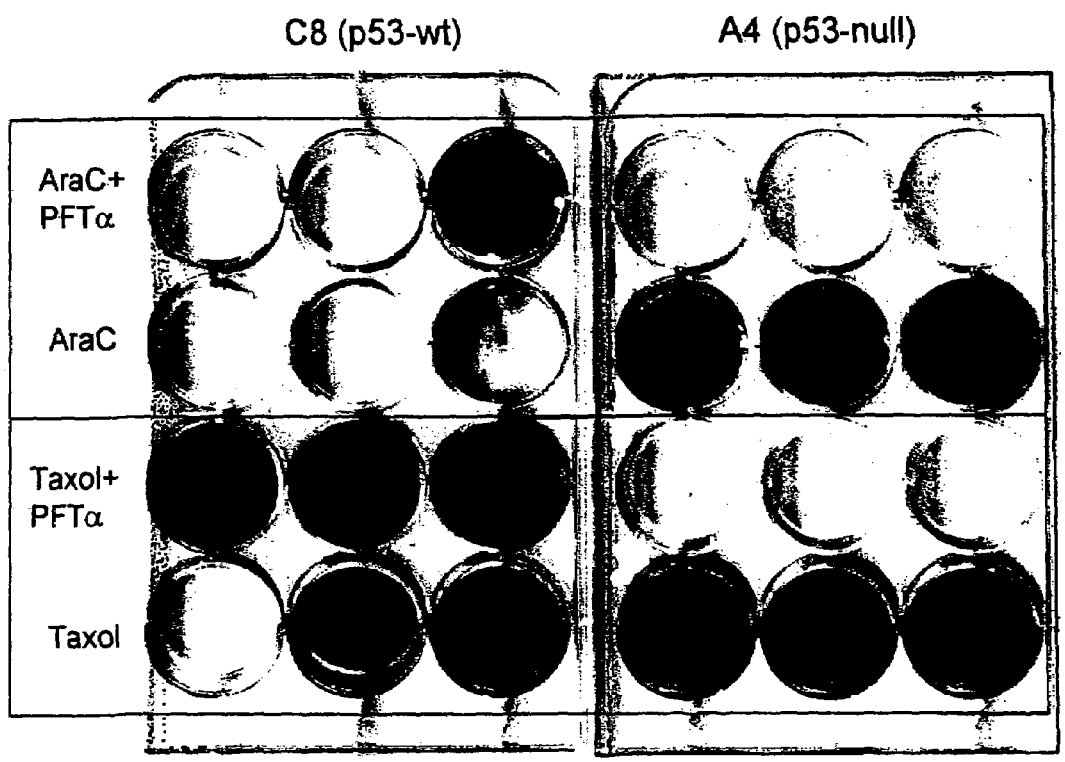
FIG. 10 illustrates the selective toxicity of PFT-α to p-53-deficient cells treated with taxol and AraC.

Identical tests were performed to show that pifithrin-alpha suppresses p53-dependent apoptosis caused by etoposide, taxol, cytosine arabinoside, UV light, and gamma radiation (see FIG. 10). The results are identical to those illustrated in FIG. 3 for doxorubicin.

With respect to tests using gamma radiation, it surprisingly was found that a compound of structural formula (I) or (II), e.g., pifithrin-alpha, does not protect p53-deficient cells (A4) from radiation, but to the contrary, at a concentration of 20 μM, potentiates radiosensitivity of p53-deficient cells. PFT-α, therefore, demonstrates the unexpected dual benefit of potentiating radiation with respect to p53-deficient cancer cells, while inhibiting p53 activity in p53-containing cells, thereby protecting such cells from the effects of radiation. FIG. 10 illustrates selective toxicity of pifithrin-alpha to p53-deficient cells treated with taxol and AraC (cytosine arabinoside). This data supports the unexpected dual effect demonstrated by PFT-α discussed above in connection with FIG. 3.

Figure 4:
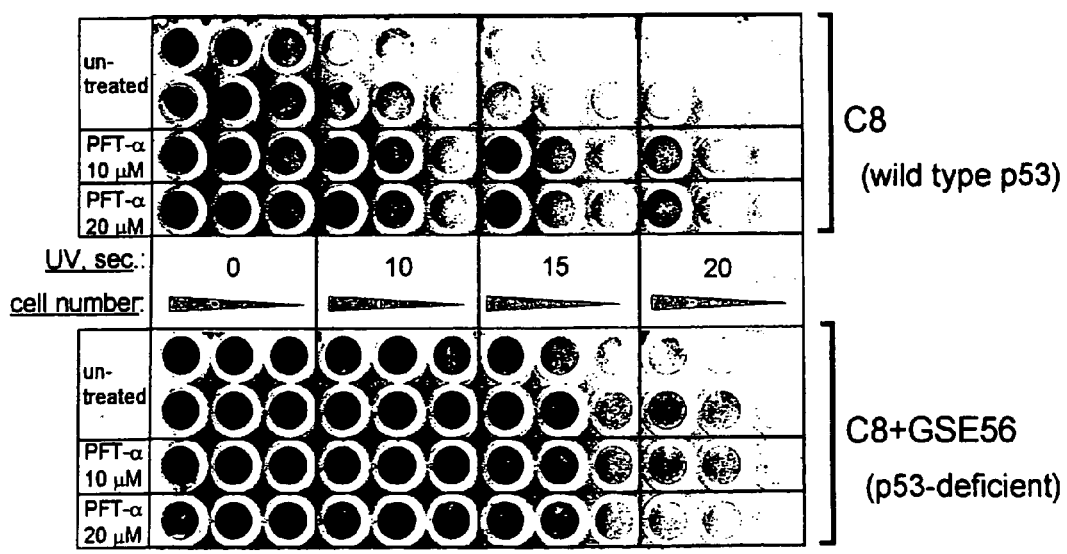
FIG. 4 illustrates the specificity of PFT-α for p53 wild-type cells.

FIG. 4 illustrates that the antiapoptotic activity of PFT-α is p53 dependent, i.e., PFT-α specifically effects p53 wild-type cells. Sensitivity of C8 cells to UV irradiation depends on the presence of pifithrin-alpha, while the sensitivity of C8 having p53 inactivated by GSE56 (a dominant negative mutant) did not depend on the presence of PFT-α. PFT-α, therefore, has no effect on survival of p53-deficient cells after genotoxic stress.

Figure 5A:
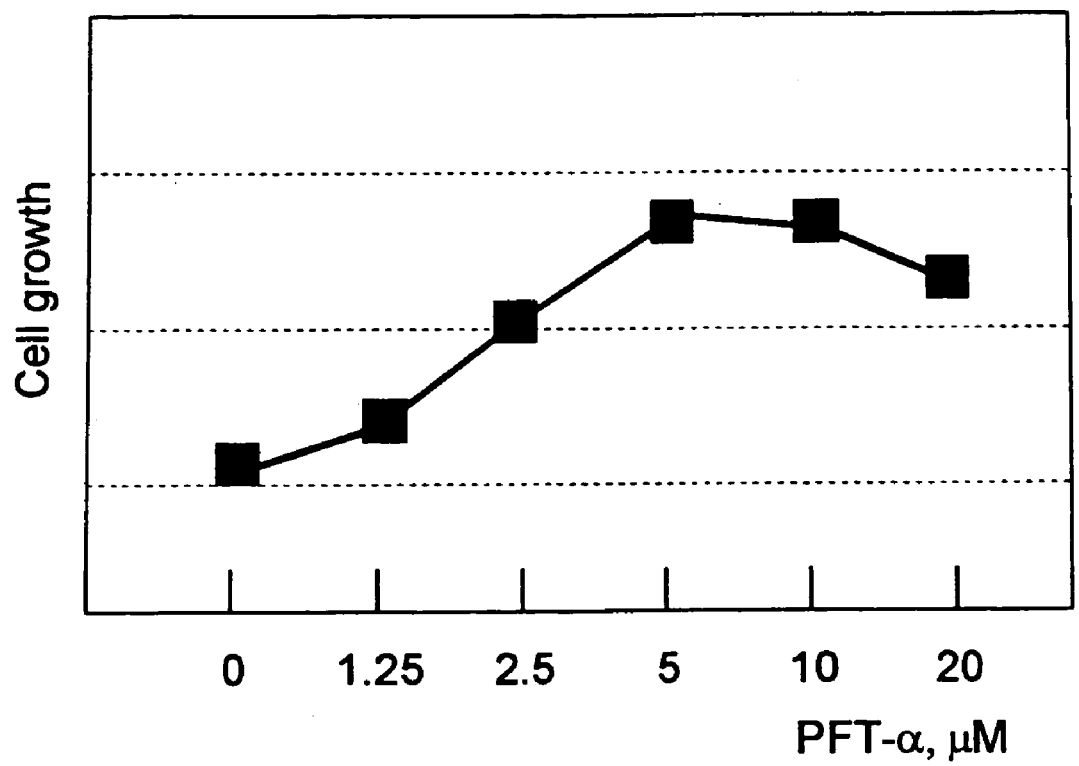
FIGS. 5(a) and (b) illustrate that PFT-α delays aging of rat embryo fibroblasts in vitro.
Figure 5B:
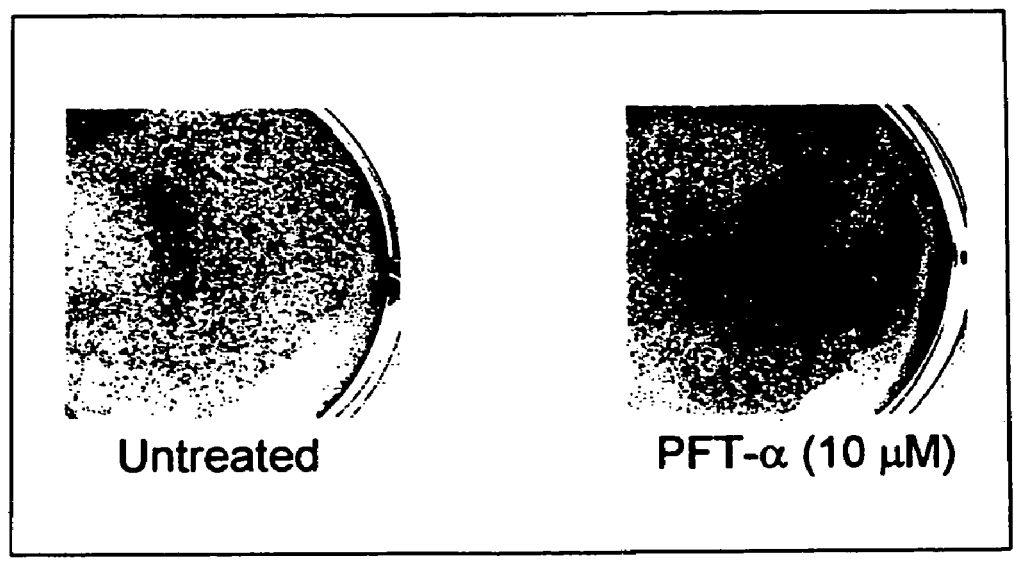

FIGS. 5(a) and (b) illustrate that pifithrin-alpha delays aging of rat embryo fibroblasts in vitro, i.e., growth stimulation of presenescent cells by the indicated concentrations of pifithrin-alpha during 3 days of cell growth. In FIG. 5(a), cell growth is presented relative to the number of plated cells.

FIG. 6 shows the effects of PFT-α on the p53 pathway and at which stage in the pathway PFT-α targets p53. FIG. 6(a) demonstrates that PFT-α inhibits apoptosis in Saos-2 cells transiently expressing p53. Cells were transfected with the plasmid DNA expressing green fluorescent protein (GFP) with the 5× excess of the plasmid carrying either wild-type human p53 (middle and bottom) or with no insert (top). Transfected cells were maintained with (bottom) or without (top and middle) PFT-α. The majority of fluorescent cells transfected with p53-expressing plasmid undergo apoptosis 48 hours after transfection (middle). Apoptosis was inhibited in the presence of PFT-α (bottom).

Figure 6A:
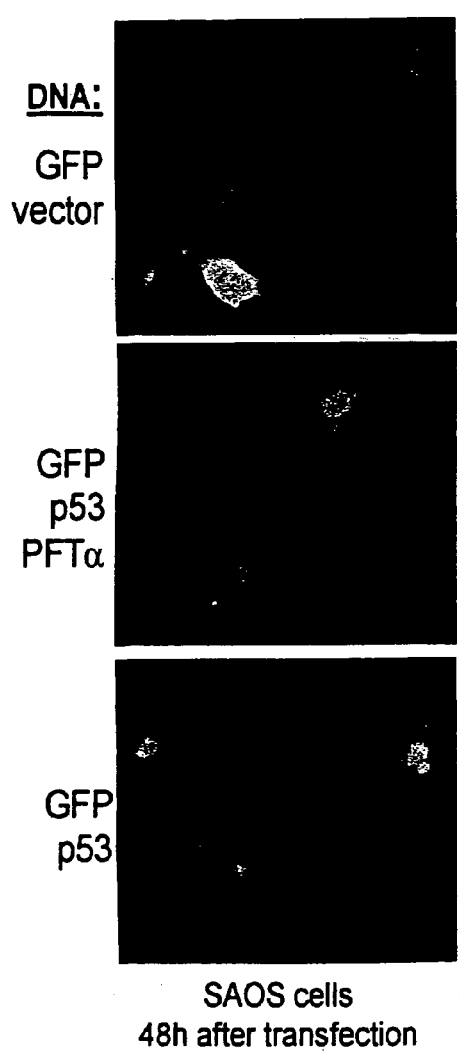
FIGS. 6(a)–(e) illustrate the effects of PFT-α on the p53 pathway.
Figure 6B:
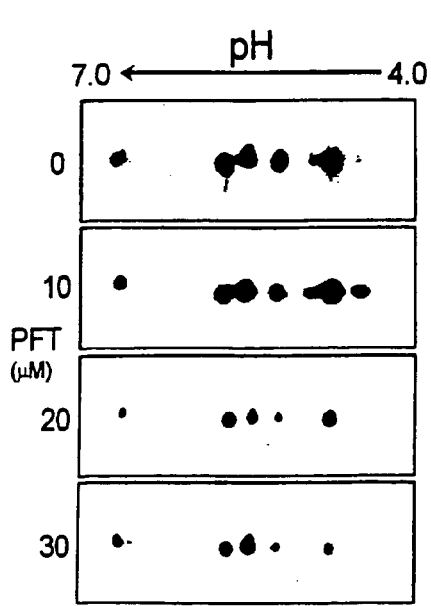
Figure 6C:
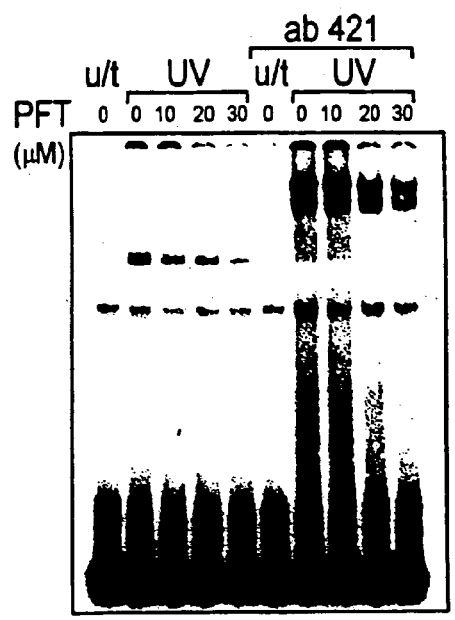

FIG. 6(b) shows a comparison of spectra of p53 protein variants in the lysates of UV-irradiated (25 J/m$^2$) ConA cells in the presence of different concentrations of PFT-α (0, 10, 20, and 30 μM) using two-dimensional protein gel electrophoresis. FIG. 6(c) shows that PFT-α partially, and in a dose-dependent manner, inhibits p53 accumulation in ConA cells after UV treatment (results of protein immunoblotting). PFT-α was added to the cells before UV treatment and total cell lysates were prepared 18 hours later.

Figure 6D:
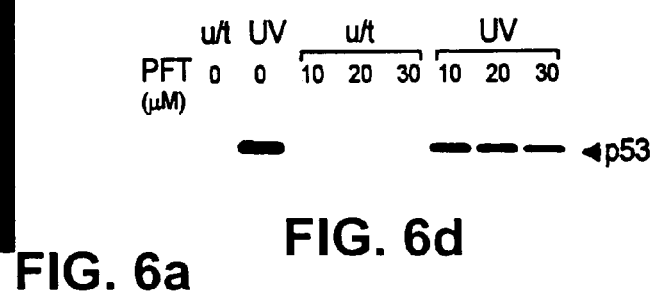
Figure 6E:
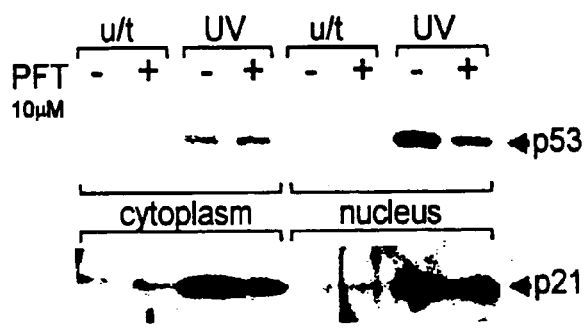

FIG. 6(d) illustrates that PFT-α changes the nuclear and cytoplasmic distribution of p53. Nuclear and cytoplasmic fractions were isolated from UV-treated ConA cells 6 hours after UV irradiation. p53 and p21$^{waf1}$ proteins were detected by immunoblotting. The nuclear and cytoplasmic ratios of p53, but not p21$^{waf1}$, were significantly decreased in the PFT-α-treated cells. FIG. 6(e) shows that PFT-α does not affect DNA-binding activity of p53. In particular, results of a gel shift assay using cell lysates from either untreated or UV-irradiated ConA cells grown in medium containing PFT-α are shown. The right-half of the gel shows a supershift of the p53-binding DNA fragment by monoclonal antibody Pab421. The decline in the amount of bound DNA is proportional to the overall decrease in p53 content in the presence of PFT-α.

The results in FIG. 6(a) suggest that PFT-α acts downstream of p53. FIGS. 6(b)–(e) suggest that PFT-α did not alter phosphorylation or sequence-specific DNA binding of p53 in ConA cells after DNA-damaging treatments, as judged by protein immunoblotting in combination with two-dimensional protein analysis and gel shift assays. However, PFT-α slightly lowered the levels of nuclear, but not cytoplasmic, p53 induced by UV irradiation. In contrast, PFT-α did not affect the nuclear-cytoplasmic ratio of the p53-inducible p21$^{waf1}$ protein. These results illustrate that PFT-α can modulate the nuclear import or export, or both, of p53, or can decrease the stability of nuclear p53.

FIG. 7(a)–(d) shows the in vivo effect of a single injection of PFT-α on the sensitivity of mice to lethal doses of radiation. In particular, FIG. 7 illustrates that pifithrin-alpha protects mice from radiation-induced death. In this test, two different strains of mice (C57BL and Balb(c)) were treated with lethal and sublethal doses of whole-body gamma radiation. A comparison was made between (i) untreated unirradiated mice, (ii) unirradiated mice that received a single intraperitoneal (i.p.) injection of PFT-α, (iii) untreated gamma-irradiated mice, and (iv) mice injected intraperitoneally with PFT-α immediately before gamma irradiation. PFT-α treatment completely rescued mice of both strains from 60% killing doses of gamma irradiation (8 Gy for C57BL and 6 Gy for Balb/c). Significant protection also was seen at higher doses of irradiation that were lethal for control animals (FIG. 7(a)–(c)). PFT-α-injected mice lost less weight than irradiated mice that were not pretreated with the drug (FIG. 7(d)). PFT-α did not protect p53-null mice from lethal irradiation, which confirmed that PFT-α acts through a p53-dependent mechanism in vivo.

In the plots of FIG. 7, whole-body gamma irradiated mice (60 total) were divided into four groups. Ten mice from each group were injected i.p. with pifithrin-alpha (2.2 mg/kg) five minutes prior to irradiation. Ten mice of each group did not receive an injection of PFT-α. FIG. 7 shows the survival curve for the mice in each of the above three groups. The data in FIG. 7 shows that temporary p53 inhibitor is an effective radioprotector and that PFT-α has a strong rescuing effect in both mouse strains. PFT-α injection abrogated the gradual loss of weight by C57BL6 mice after 8 Gy of gamma irradiation (the observed increase in the weight of the nonirradiated mice reflects the normal growth of young 5-week-old animals). The experiments were repeated at least three times with 10 mice per each experimental subgroup.

Figure 8:
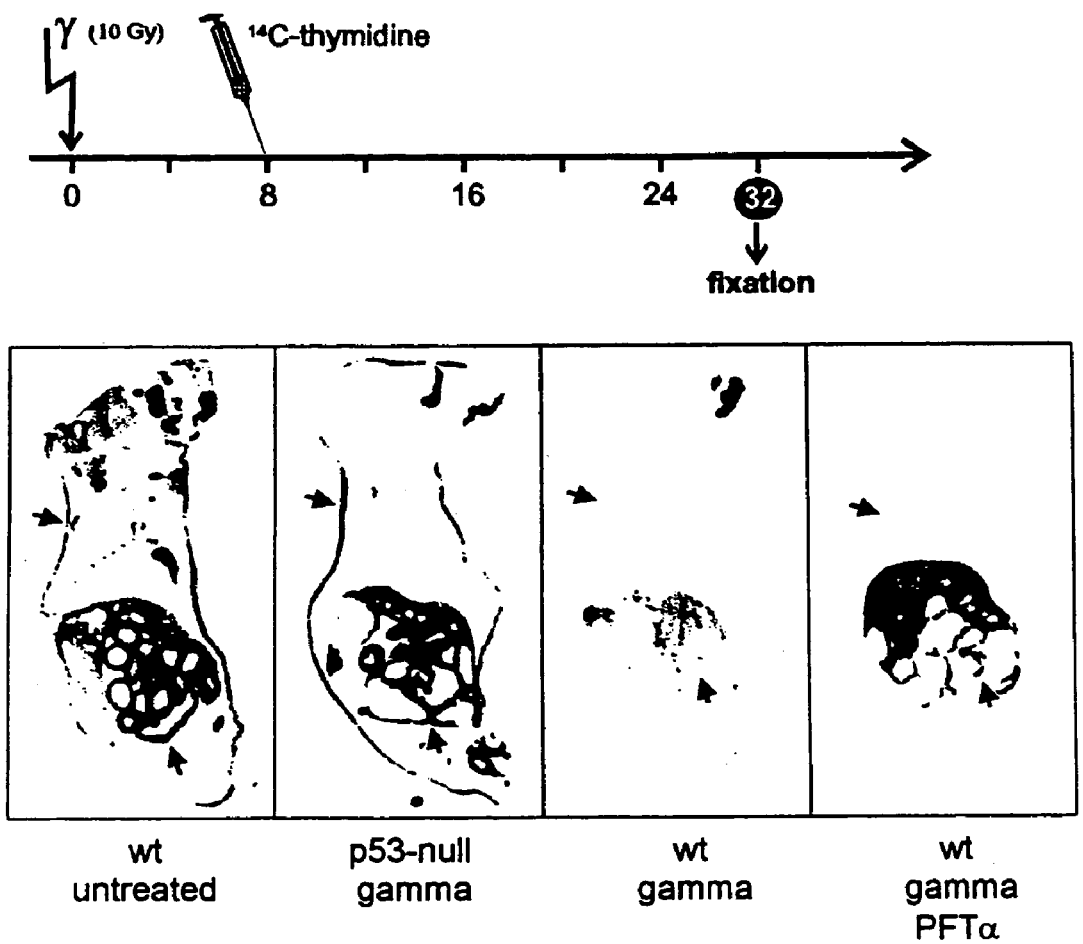
FIG. 8 contains autoradiograms illustrating the effects of PFT-αin blocking p53-mediated growth arrest in vivo.

FIG. 8 illustrates that pifithrin-alpha is capable of blocking p53-mediated growth arrest in vivo in the mouse (single intraperitoneal injection, 2.2 mg/kg). Four-week-old p53-deficient mice and p53 wild-type (wt) mice were whole body gamma irradiated (10 Gy). Pifithrin-alpha was injected in one of the p53 wild-type animals five minutes before irradiation. $^{14}$C-thymidine (10 mCi per animal) was injected intraperitoneally into each mouse 8 hours after irradiation. The mice were sacrificed 24 hours after irradiation and whole body sectioned (25 μm thick) using cryostatic microtome were prepared and exposed to X-ray film to monitor the distribution of $^{14}$C in the tissue. FIG. 8 presents autoradiograms of representative sections. Arrows indicate $^{14}$C-thymidine incorporation in the skin and intestine. The test showed that an injection of PFT-α inhibits apoptosis in the skin and small intestine of gamma-irradiated mice.

FIG. 8 shows that $^{14}$C labeling of skin, intestine, and several other tissues was significantly decreased after gamma irradiation in p53+/+ mice but not p53−/− mice, reflecting the p53 dependence of the effect. The radiation-induced decrease in $^{14}$C-thymidine incorporation was less pronounced in PFT-α-treated mice than in control irradiated animals, reflecting PFT-α inhibition of p53 activity. These results illustrate that PFT-α attenuates the p53-dependent block of DNA replication in rapidly proliferating tissues after whole-body gamma irradiation.

Figure 9:
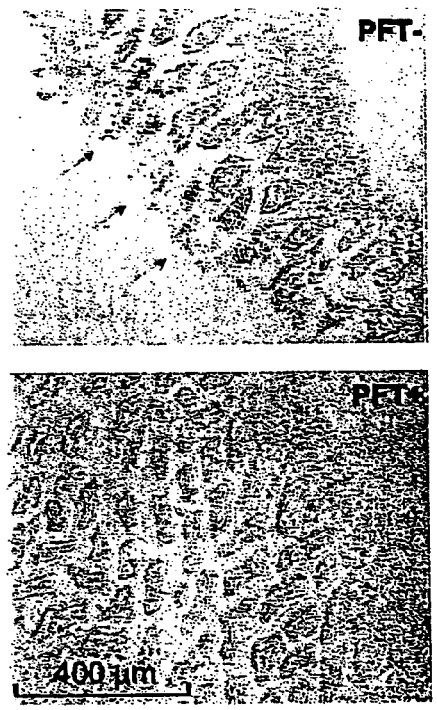
FIG. 9 shows the small intestine of p53 wild-type mice 24 hours after whole-body gamma radiation.

FIG. 9 contains photographs comparing tissue morphology and apoptosis (TUNEL staining) in the epithelium of the small intestine of C57BL6 wild-type mice (PFT-treated (+) and untreated (−)) 24 hours after 10 Gy of whole-body gamma irradiation. Areas of massive apoptosis are indicated by the arrows. The extensive apoptosis observed in the crypts and villi of the small intestine was abrogated in mice treated with PFT-α before irradiation, which correlates with the changes in thymidine incorporation illustrated in FIG. 8.

Figure 11B:
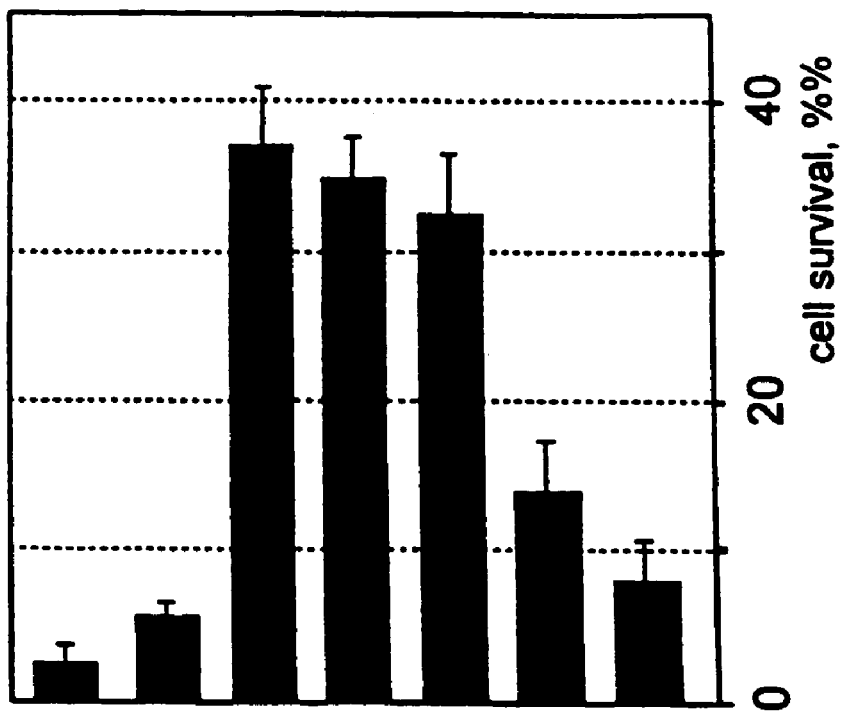
FIGS. 11(a) and (b) show the effect of PFT-α, and time of application, on the survival of C8 cells after UV radiation.
Figure 11A:
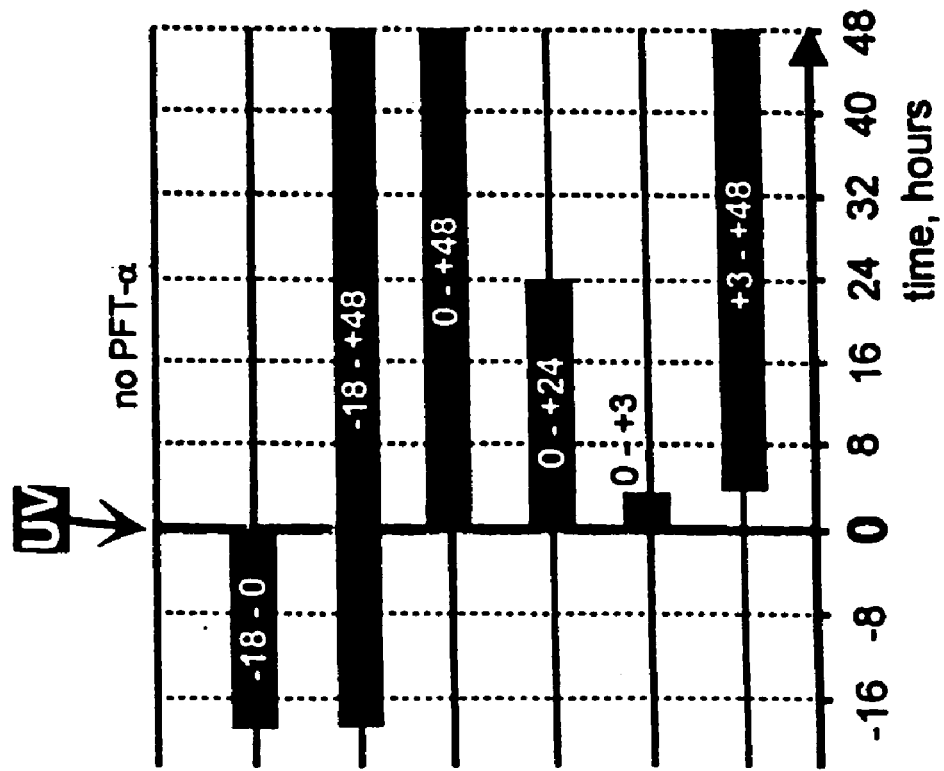

FIG. 11 shows the dependence of C8 cell survival after UV irradiation on the time and duration of PFT-α application. FIG. 11 includes a comparison of anti-apoptotic effect of PFT-α added at different time intervals to C8 cells treated with UV radiation. (25 J/m$^2$). Ten µM of PFT-α were added to the culture media at different time intervals (FIG. 11(a)). The proportions of surviving cells were estimated using MTT assay 48 hours after UV treatment and are shown in FIG. 11(b).

FIGS. 11(a) and (b) show that PFT-α had little to no protective effect where administered before (up to 18 hours) and removed immediately before UV treatment of C8 cells. However, a short 3-hour incubation with PFT-α after UV treatment had a pronounced protective effect, whereas a 24-hour incubation provided maximal protection. PFT-α did not rescue UV-irradiated cells from apoptosis if PFT-α was administered three hours after UV irradiation. These results show that PFT-α can efficiently inhibit p53-dependent apoptosis and that its effects are reversible and require the presence of the temporary p53 inhibitor. Because many cells survived a lethal dose of UV irradiation after only 3 hours of incubation with PFT-α, the UV-induced apoptic death signal is significantly reduced within several hours and completely disappears within 24 hours of irradiation.

Figure 12A:
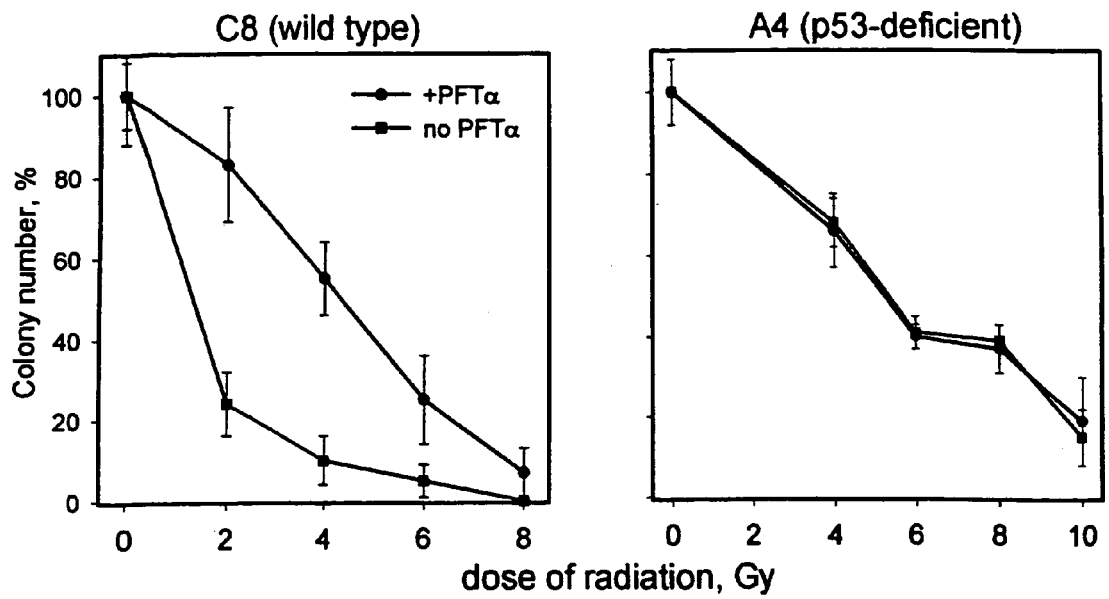
FIGS. 12(a) and (b) are plots of colony number vs. radiation dose for C8 and A4-type cells and for human diploid fibroblasts showing the effect of PFT-α.
Figure 12B:
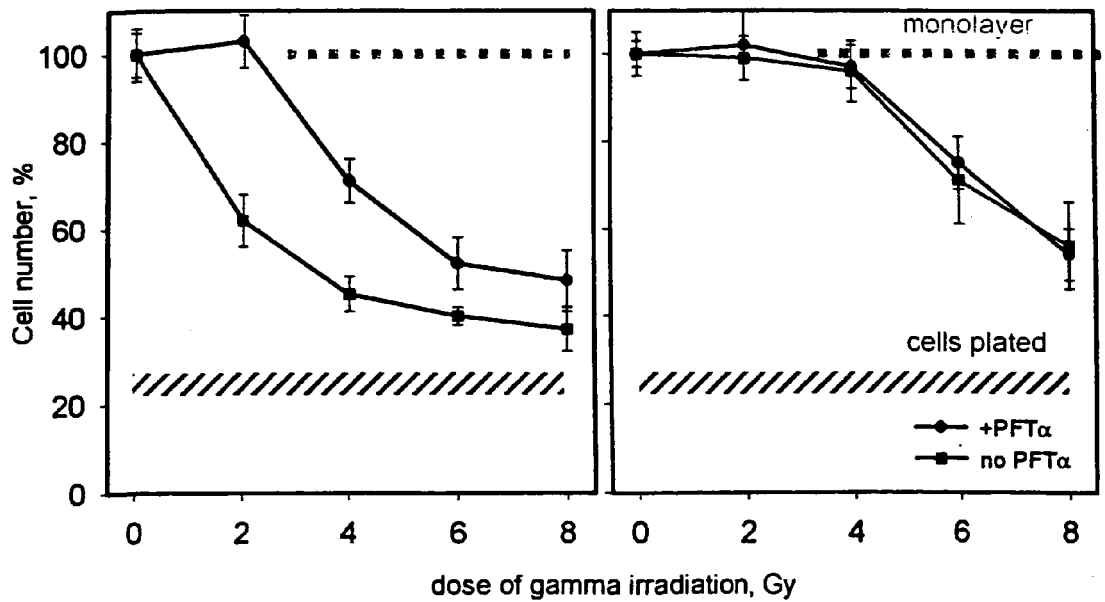

The plots of FIG. 12 show that PFT-α facilitates long-term survival of p53 wild-type cells, but not p53-deficient cells after gamma irradiation. Human diploid fibroblasts with wild-type p53, strain WI38, and p53-deficient fibroblasts from Li-Fraumeni syndrome patient, line 041, were treated with the indicated doses of gamma radiation, with or without 20 µM of PFT-α, in the medium (FIG. 12(b)). PFT-α was removed 48 hours after irradiation and the cells were allowed to grow for an additional three days. By that time, unirradiated cells reached complete monolayer. Cell numbers were estimated using crystal violet staining assay (100% corresponds to confluent cell cultures). Dashed line indicates the number of cells plated. p53-wild-type and p53-deficient mouse embryo fibroblasts (MEF) transformed with Ela+ras, lines C8 and A4, respectively, were treated with the indicated doses of gamma radiation in the presence and in the absence of 20 µM of PFT-α and replated at low density (10$^3$ cells per plate) 12 hours after irradiation (FIG. 12(a)). Numbers of growing colonies were calculated in two weeks and normalized according to the unirradiated control.

Figure 13A:
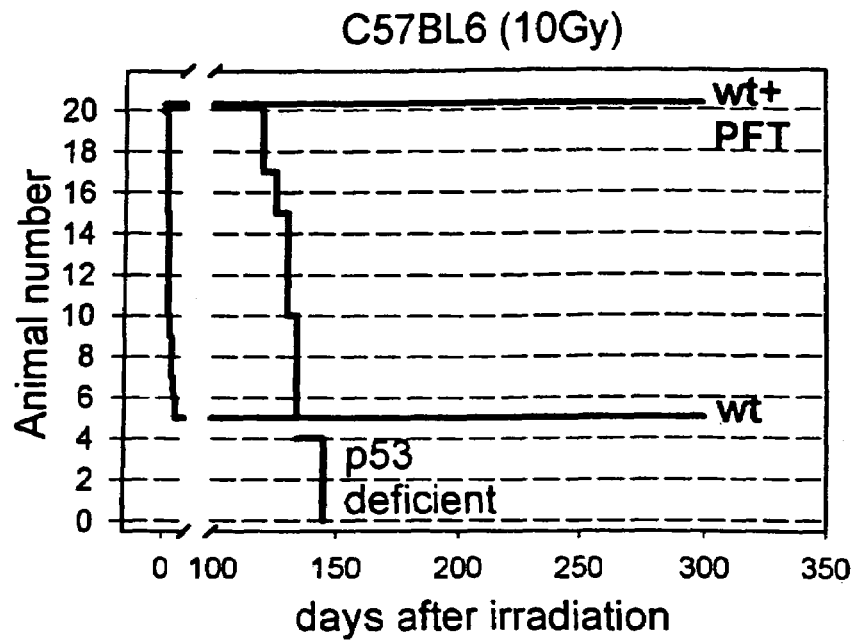
FIGS. 13(a) and (b) are plots of number of animals vs. days after irradiation showing that PFT-α and PFT-β treated animals are not accompanied by accelerated cancer development.
Figure 13B:
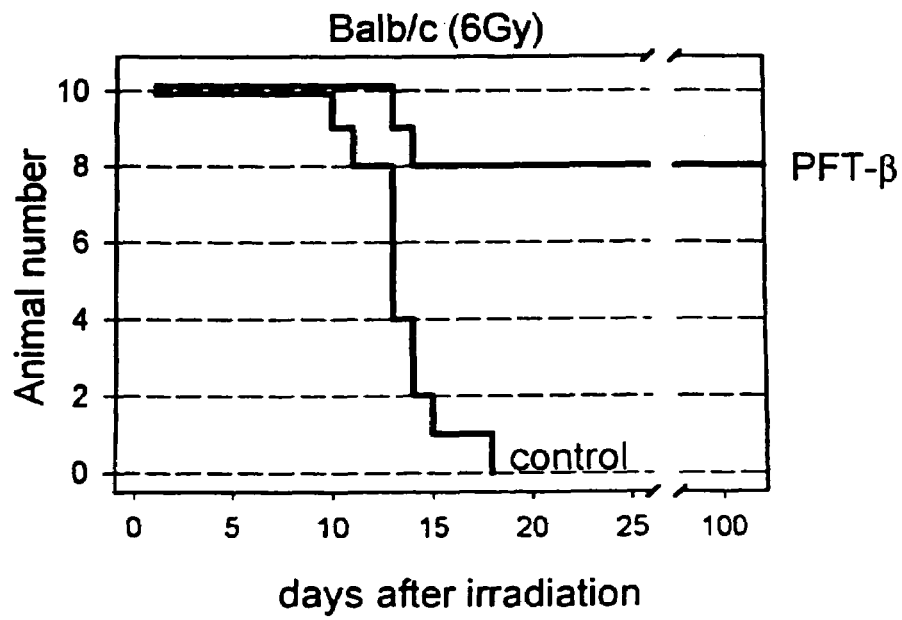

FIG. 13(a) shows the effect of PFT-α on mice subjected to whole body radiation. Both wild-type (wt) mice and p53-deficient mice were irradiated. One group of the wild-type mice were treated with PFT-α. FIG. 13(a) shows that the PFT-α treated mice survived 300 days after radiation. In contrast, fifteen untreated wild-type mice died within 100 days. The p53-deficient mice were unaffected for about 125 days, then all expired over the next 25–30 days. FIG. 11(b) shows similar protective effects for PFT-β.

Figure 14:
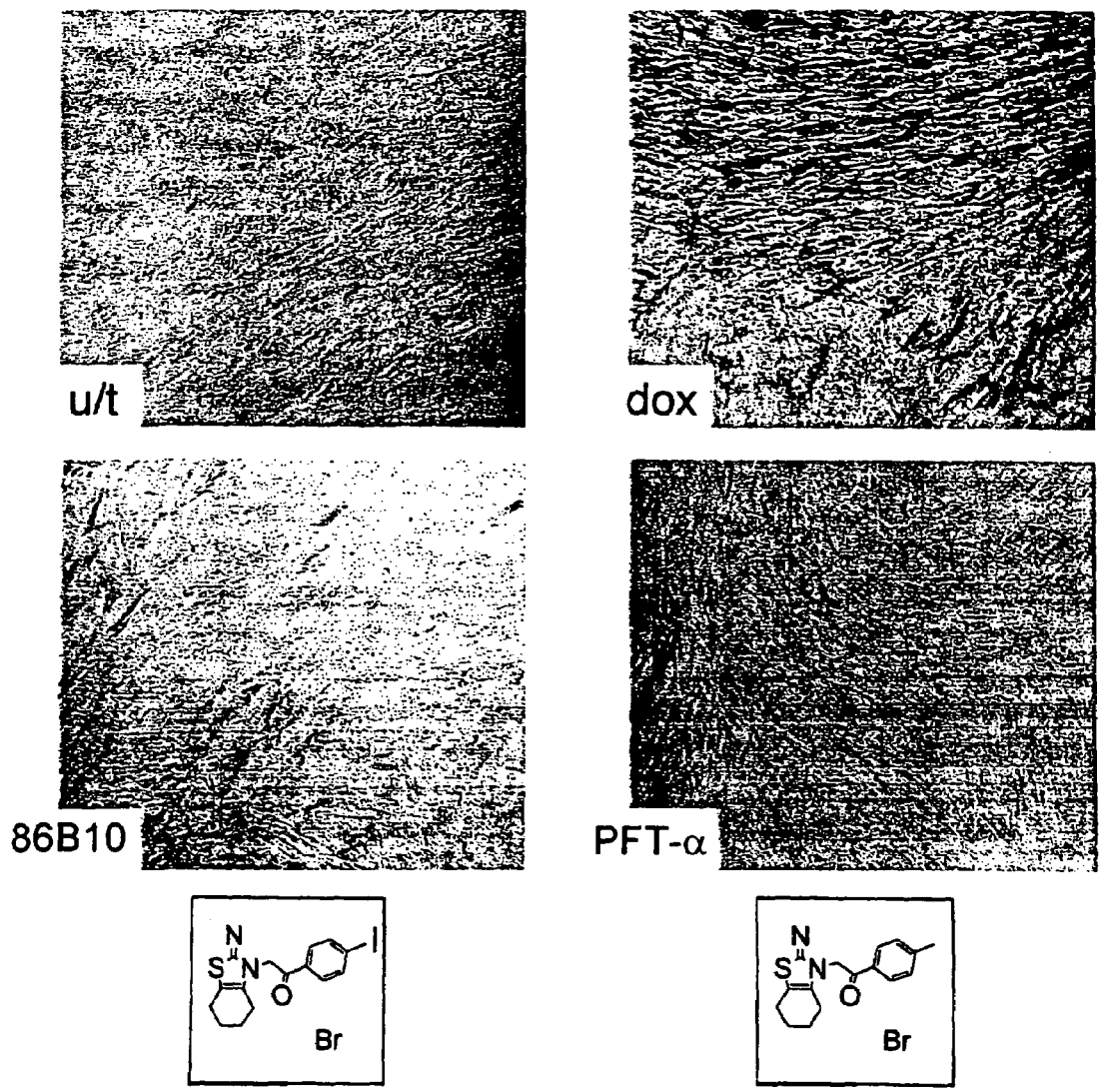
FIG. 14 illustrates p53 suppression by PFT-α and 86B10 in ConA cells treated with doxorubicin.

FIG. 14 contains microphotographs of ConA cells stained with X-gal, and illustrates test results for pifithrin-alpha and 86B10 in a p53 suppression in ConA cells treated with doxorubicin. 86B10 displays a similar, but weaker, p53-inhibition, effect than PFT-α.

Figure 15:
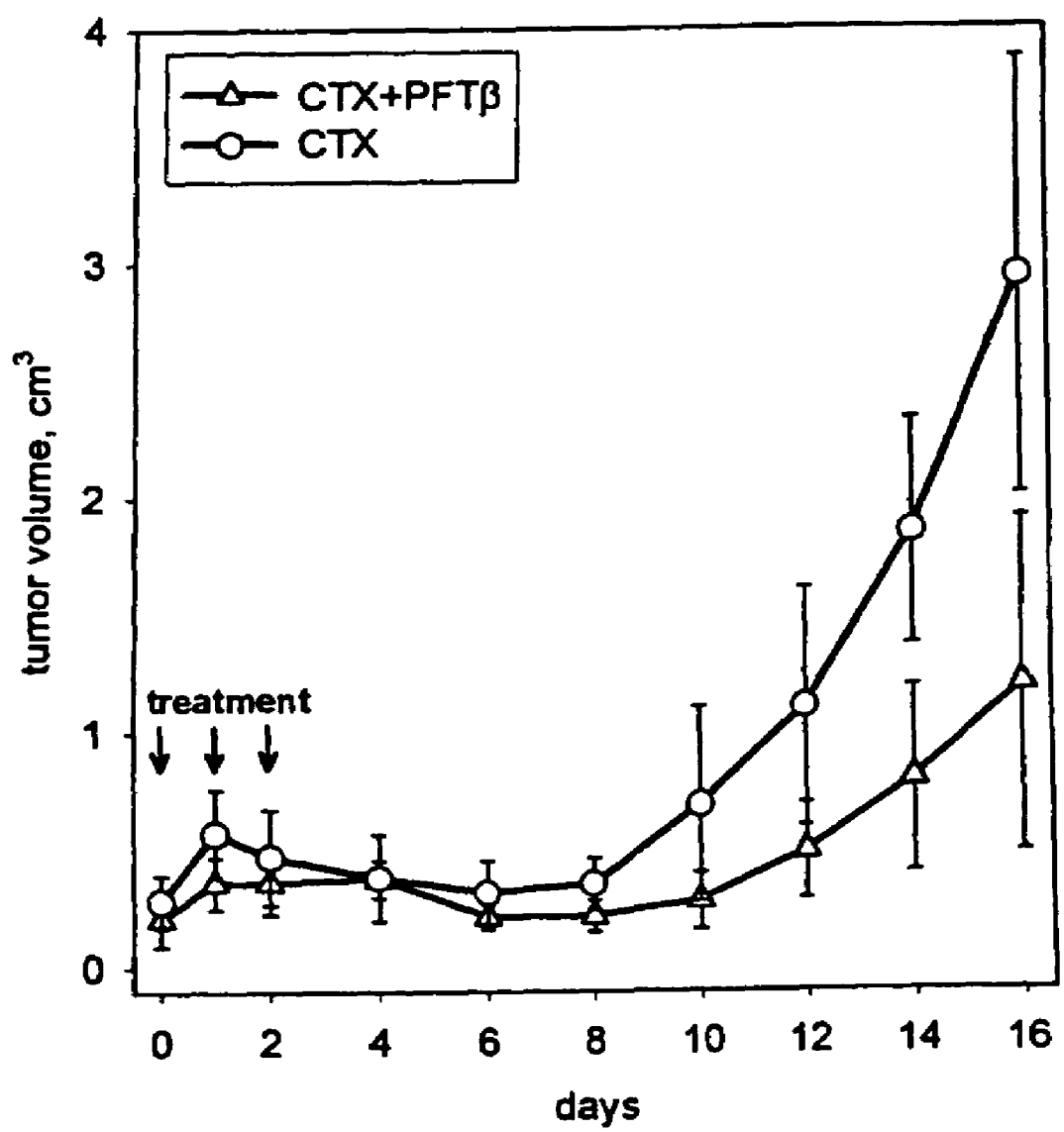
FIG. 15 is a plot of tumor volume vs. days for C57BC mice subjected to treatment with cyclophosphamide, with and without administration of PFT-β.

FIG. 15 is a plot of tumor volume vs. days for C57BL mice treated with cyclophosphamide (CTX), with and without administration of PFT-β. The mice were treated with CTX at days 0, 1, and 2, and tumor volume was monitored for sixteen days. Mice treated with PFT-β exhibited a substantial decrease in tumor growth.

Figure 16:
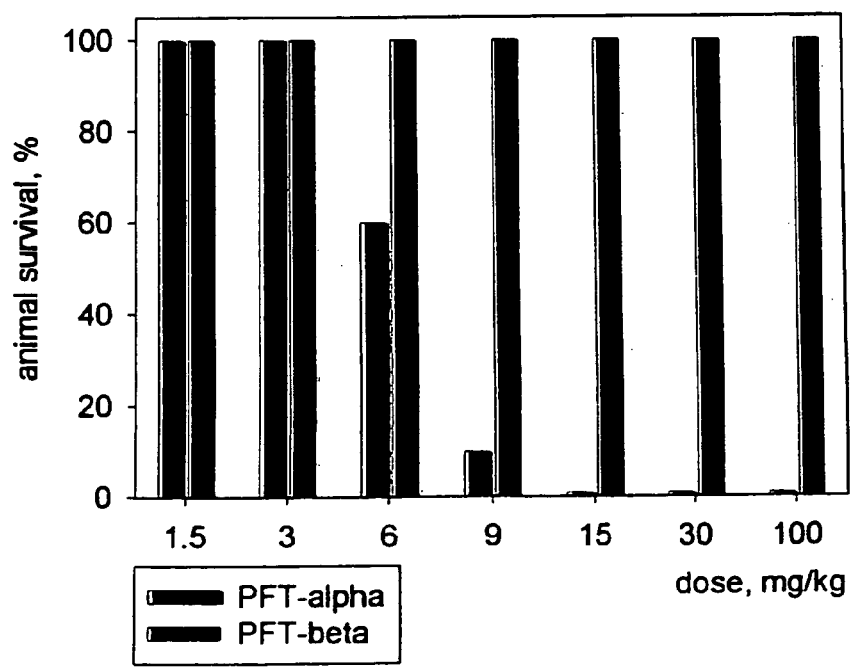
FIG. 16 compares the toxicity of PFT-α to PFT-β.

As previously stated, the tests and experiments set forth in FIGS. 1–15 using PFT-α were repeated using PFT-β. The results from the tests using PFT-β were essentially identical to the results from the tests using PFT-α. However, PFT-β is a preferred temporary p53 inhibitor because the toxicity of PFT-β is substantially lower than the toxicity of PFT-α, as illustrated in FIG. 16.

The above tests and experiments show that temporary p53 inhibitors, like PFT-α and PFT-β, act downstream of p53 activation. PFT-α and PFT-β also do not effect either post-translational modifications of p53 or the DNA binding affinity of p53. Importantly, the tests show that PFT-α and PFT-β, and other temporary p53 inhibitors, reduce nuclear accumulation of p53, which serves as the basis for use of a temporary p53 inhibitor, such as a compound of structural formulae (I) through (IV), in therapy.

Suppression of p53 typically results in the survival of cells that otherwise are eliminated by p53, which can increase the risk of new cancer development. For example, p53-deficient mice are extremely sensitive to radiation-induced tumorigenesis. However, no tumors or any other pathological lesions were found in a group of 30 survivors rescued from lethal gamma irradiation by PFT-α seven months after irradiation. Thus, temporary suppression of p53 activity is different from p53 deficiency in terms of cancer predisposition.

A temporary p53 inhibitor, like a compound of structural formulae (I) through (IV), effectively and reversibly inhibits p53 functions. Accordingly, a temporary p53 inhibitor can be applied to rescue cells having p53 from apoptic death or irreversible growth arrest caused by genomic stress. Importantly, the cellular effects of a temporary p53 inhibitor are reversible, and short-lasting, therefore, p53 suppression requires an essentially constant presence of the inhibitor. Furthermore, the in vivo effects of a present inhibitor are dependent on the presence of p53.

The compounds of structural formulae (I) through (IV), and especially PFT-α and PFT-β, (a) suppress p53-dependent radiation-induced growth arrest in rapidly proliferating mouse tissues, (b) rescue mice from lethal doses of gamma radiation using a single i.p. injection, (c) reduce the toxicity of chemotherapeutics, (d) do not reduce the efficacy of chemo- or radiation therapy of p53 deficient mouse tumors, and (e) do not result in a high incidence of tumors in irradiated animals, thereby illustrating the therapeutic use of a temporary p53 inhibitor.

The above-described tests using PFT-α and PFT-β illustrate the therapeutic use of temporary p53 inhibitors to reduce the side effects of radiation therapy or chemotherapy for human cancers that have lost functional p53. Because the effects of PFT-α and PFT-β are p53 dependent, the compounds do not affect the sensitivity of such tumors to treatment. In fact, i.p. injection of PFT-α did not change the radiation response of p53-deficient tumor xenografts in $p53^{+/+}$ nude mice.

The temporary p53 inhibitors, like compounds of structural formulae (I) through (IV), therefore, can be used in the following applications, for example, (a) a therapy using p53 suppression to reduce pathological consequences of tissue response to variety of stresses associated with p53 activity (e.g., anticancer radio- and chemotherapy, ischemias, stroke, hyperthermia, etc.);

(b) application of a temporary p53 inhibitor, such as a compound of structural formulae (I) through (IV), e.g., a compound of structural formula (V) or (VI), as a tool for investigating p53 pathway analysis and modulation;

(c) administration of a temporary p53 inhibitor, such as a compound of structural formulae (I) through (IV), as a drug for rescuing cells from death after a variety of stresses;

(d) administration of a temporary p53 inhibitor, such as a compound of structural formulae (I) through (IV), as a drug for sensitizing p53-deficient cells to anticancer therapy;

(e) administration of a temporary p53 inhibitor, such as a compound of structural formulae (I) through (IV), as a potential antisenescence drug to suppress tissue aging;

(f) application of a temporary p53 inhibitor, such as a compound of structural formulae (I) through (IV), to suppress p53-dependent transactivation as a tool for p53 pathway analysis and modulation;

(g) administration of a temporary p53 inhibitor, such as a compound of structural formulae (I) through (IV), as a radiation protector in vivo; and (h) administration of a temporary p53 inhibitor, such as a compound of structural formulae (I) through (IV), in vivo, to protect cells from a variety of stresses in different pathological circumstances, including side effects of anticancer therapy, acute inflammations, injuries (e.g., burns and central nervous system injuries), cell aging, hyperthermia, seizures, transplant tissues and organs prior to transplanting, preparation of a host for a bone marrow transplant, and hypoxias (e.g., ischemia and stroke).

Obviously, many modifications and variations of the invention as hereinbefore set forth can be made without departing from the spirit and scope thereof and, therefore, only such limitations should be imposed as are indicated by the appended claims.

What is claimed is:

1. A method of reducing hair loss associated with a cancer therapy comprising administering a therapeutically effective dose of a reversible p53 inhibitor to a mammal in need thereof in conjunction with the cancer therapy.

2. The method of claim 1 wherein the cancer therapy comprises radiation therapy.

3. The method of claim 1 wherein the cancer therapy comprises chemotherapy.

4. The method of claim 1 wherein the therapeutically effective dose is administered topically.

5. The method of claim 1 wherein the therapeutically effective dose is administered transdermally.

* * * * *